(12) United States Patent
Wu et al.

(10) Patent No.: US 7,144,881 B2
(45) Date of Patent: Dec. 5, 2006

(54) ARYLCYCLOPROPYLCARBOXYLIC AMIDES AS POTASSIUM CHANNEL OPENERS

(75) Inventors: Yong-Jin Wu, Madison, CT (US); Alexandre L'Heureux, Longueuil (CA); Li-Qiang Sun, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 302 days.

(21) Appl. No.: 10/719,184

(22) Filed: Nov. 21, 2003

(65) Prior Publication Data

US 2004/0110754 A1    Jun. 10, 2004

Related U.S. Application Data

(60) Provisional application No. 60/428,337, filed on Nov. 22, 2002.

(51) Int. Cl.
| | |
|---|---|
| A61K 31/535 | (2006.01) |
| C07D 265/30 | (2006.01) |
| C07D 211/72 | (2006.01) |
| C07D 307/78 | (2006.01) |
| C07C 239/00 | (2006.01) |

(52) U.S. Cl. .................. 514/237.8; 514/357; 514/429; 514/468; 514/620; 544/169; 546/312; 548/567; 549/469; 564/164

(58) Field of Classification Search ............. 514/237.8, 514/429, 468, 357, 620; 544/169; 548/567; 546/312; 549/469; 564/164
See application file for complete search history.

(56) References Cited

U.S. PATENT DOCUMENTS

| | | | |
|---|---|---|---|
| 4,927,838 | A | 5/1990 | Guthrie et al. |
| 6,046,239 | A | 4/2000 | Lennox et al. |
| 6,413,995 | B1 | 7/2002 | Hasegawa et al. |

FOREIGN PATENT DOCUMENTS

| | | |
|---|---|---|
| EP | 810220 A1 | 12/1997 |
| JP | 45-14291 | 5/1970 |
| JP | 2-138159 | 5/1990 |
| WO | 00/07993 | 2/2000 |
| WO | 00/42013 | 7/2000 |
| WO | 01/10380 | 2/2001 |
| WO | 01/10381 | 2/2001 |

OTHER PUBLICATIONS

Valentine Gribkoff, The therapeutic potentila of neuronal KCNQ channel modulaters; Central & Peripheral Nervous System; Review; Expert Opinion Therapeutic Targets, 2003: pp. 737-748.*
Wang, S., et al. "KCNQ2 and KCNQ3 Potassium Channel Subunits: Modular Correlates of the M-Channel", *Science*, pp. 282, 1890-1893 (1998).

* cited by examiner

*Primary Examiner*—Golam M. M. Shameem
*Assistant Examiner*—Ebenezer Sackey
(74) *Attorney, Agent, or Firm*—Aldo A. Algieri

(57) ABSTRACT

The present invention provides novel arylcyclopropylcarboxylic amides and related derivatives having the general Formula I

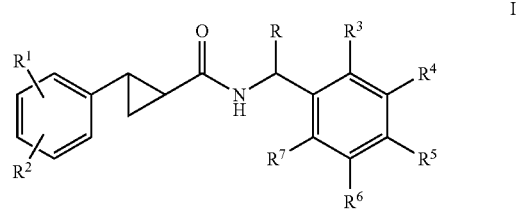

wherein R, $R^1$, $R^2$, $R^3$, $R^4$, $R^5$, $R^6$ and $R^7$ are as defined in the specification, or a nontoxic pharmaceutically acceptable salt, solvate or hydrate thereof which are openers or activators of KCNQ potassium channels. The present invention also provides pharmaceutical compositions comprising said arylcyclopropylcarboxylic amides and to the method of treatment of disorders sensitive to KCNQ potassium channel opening activity such as migraine or a migraine attack, bipolar disorders, epilepsy, acute and chronic pain and anxiety.

7 Claims, No Drawings

ARYLCYCLOPROPYLCARBOXYLIC AMIDES AS POTASSIUM CHANNEL OPENERS

CROSS-REFERENCE TO RELATED APPLICATIONS

This is a non-provisional application which claims the benefit of U.S. Provisional Application No. 60/428,337 filed Nov. 22, 2002.

FIELD OF THE INVENTION

The present invention is directed to novel arylcyclopropylcarboxylic amide derivatives which are modulators of KCNQ potassium channels and are therefore useful in treating disorders responsive to the modulation of the potassium channels. The present invention also provides a method of treatment with the novel arylcyclopropylcarboxylic amide derivatives and to pharmaceutical compositions thereof.

BACKGROUND OF THE INVENTION

Potassium ($K^+$) channels are considered to be the most diverse class of ion channels and have several critical roles in cell function. This has been demonstrated in neurons where $K^+$ channels are responsible, in part, for determining cell excitability by contributing to membrane repolarization following depolarization, resting membrane potential, and regulation of neurotransmitter release. The M-current has long been described, by electrophysiology recording methods and by pharmacology, as a dominant conductance in controlling neuronal excitability. Pharmacological activation or suppression of M-currents by small molecules could have profound effects in controlling neuronal excitability. Recently, Wang et al., Science, 282:1890–1893, (1998) reported that co-assembly of the KCNQ2 and KCNQ3 potassium channels underlies the native M-current in neurons.

Activation or opening of the KCNQ channel(s), particularly the KCNQ2 or KCNQ2/3 channel(s), mutated or wild type, may prove to be beneficial in increasing hyperpolarization of neurons, thereby resulting in protection from abnormal synchronous firing during a migraine attack. The present invention provides a solution to the problem of abnormal synchronous firing of neurons related to migraine headache by demonstrating that modulators, preferably openers, of KCNQ potassium channels increases hyperpolarization of neurons which protects against abnormal synchronous neuron firing involved in migraine attacks.

Although the symptom pattern varies among migraine sufferers, the severity of migraine pain justifies a need for vigorous, yet safe and effective, treatments and therapies for the great majority of cases. Needed in the art are agents that can be used to combat and relieve migraine (and diseases similar to and mechanistically related to migraine), and even prevent the recurrence of migraine. Also needed are anti-migraine agents which are effective in the treatment of acute migraine, as well as in the prodrome phase of a migraine attack. Thus, a clear goal in the art is to discover new, safe, nontoxic and effective anti-migraine compounds for use as drugs, and in anti-migraine compositions and treatments.

Because migraine afflicts a large percentage of the population, there is a need to discover compounds and agents that are useful in therapeutics and treatments, and as components of pharmaceutical compositions, for reducing, ameliorating, or alleviating the pain and discomfort of migraine headache and other symptoms of migraine. The present invention satisfies such a need by providing compounds that function as openers of the KCNQ family of potassium channel proteins to serve as anti-migraine agents or drugs and to comprise compositions to treat migraine, as described herein.

A broad range of cinnamide compounds are known and new compounds continue to be reported with a broad range of utility. Some of these compounds can be found in the disclosures of WO 00/07993 published Feb. 17, 2000, EP 810220A1, published Dec. 3, 1997, U.S. Pat. No. 4,927,838 issued May 22, 1990 to Guthrie, et al., U.S. Pat. No. 6,046,239 issued Apr. 4, 2000 to Lennox, et al., WO 00.42013, published Jul. 20, 2000, WO 01/10381 published Feb. 15, 2001, WO 01/10380 published Feb. 15, 2001, JP45-14291 published May 21, 1970, and JP2-138159 published May 28, 1990. The compounds described in these patents are distinct from those of the present invention.

SUMMARY OF THE INVENTION

The present invention provides novel arylcyclopropylcarboxylic amides and related derivatives having the general Formula I

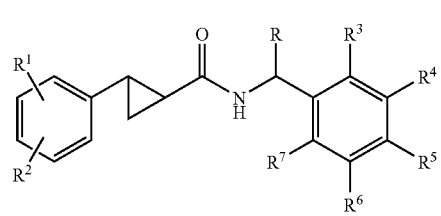

wherein R, $R^1$, $R^2$, $R^3$, $R^4$, $R^5$, $R^6$ and $R^7$ are as defined below, or a nontoxic pharmaceutically acceptable salt, solvate or hydrate thereof which are openers or activators of KCNQ potassium channels. The present invention also provides pharmaceutical compositions comprising said arylcyclopropylcarboxylic amides and to the method of treatment of disorders sensitive to KCNQ potassium channel opening activity such as migraine or a migraine attack, bipolar disorders, epilepsy, acute and chronic pain and anxiety.

DETAILED DESCRIPTION OF THE INVENTION

The present invention provides novel arylcyclopropylcarboxylic amides and related derivatives which are modulators of the KCNQ potassium channels and which have the general Formula I or a pharmaceutically acceptable salt thereof

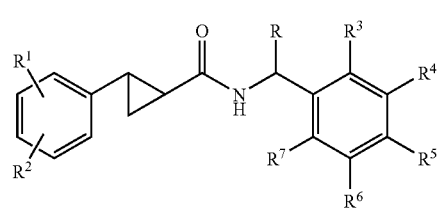

wherein R is $C_{1-4}$ alkyl, $CF_3$ or hydroxymethyl; $R^1$ and $R^2$ are each independently hydrogen, $C_{1-4}$ alkyl, halogen or morpholin-4-yl; $R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro; $R^5$ is hydrogen or fluoro; or $R^4$ and $R^5$ taken together are —CH=CH—CH=CH— or —CH$_2$CH$_2$O—; and $R^3$, $R^6$ and $R^7$ are each independently selected from hydrogen or fluoro, which are openers of the KCNQ potassium channels and are useful in the treatment of disorders which are responsive to the opening of the KCNQ potassium channels.

The present invention also provides a method for the treatment or alleviation of disorders associated with KCNQ potassium channel polypeptides and, in particular, human KCNQ potassium channel polypeptides in a mammal in need thereof which comprises administering together with a conventional adjuvant, carrier or diluent a therapeutically effective amount of a compound of Formula I or a pharmaceutically acceptable salt thereof. Preferably, the compounds of Formula I are useful in the treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

The term "pain" as used herein and in the claims means all types of acute and chronic pain, such as neuropathic pain, post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis and the term also is intended to include nociceptive pain or nociception.

The term "$C_{1-4}$ alkyl" as used herein and in the claims means straight or branched chain alkyl groups such as methyl, ethyl, propyl, isopropyl, butyl, isobutyl, and tert-butyl. The term "$C_{1-4}$ alkoxy" as used herein and in the claims means an oxygen substituted with straight or branched chain alkyl groups and includes groups such as methoxy, ethoxy, propoxy, isopropoxy, butoxy, isobutoxy, and tert-butoxy. The term "halogen" as used herein and in the claims is intended to include bromine, chlorine, iodine and fluorine.

As the compounds of the present invention contain a substituted cyclopropyl group as part of the structure, the compounds of the invention exist in either of two geometric isomeric forms, namely as cis or trans isomers. Preferred are the trans isomers in which the aryl group and the amide group, C(O)NH, are trans to each other. As the compounds of the present invention possess an asymmetric carbon atom, such as the carbon adjacent to the amide nitrogen and to which the phenyl is attached, the present invention includes the racemate as well as the individual enantiomeric forms of the compounds of Formula I as described herein and in the claims. Preferred embodiments of compounds of Formula I include the racemate, a single enantiomer, and in certain instances a single enantiomer wherein the carbon adjacent to the amide nitrogen and to which the phenyl is attached has the (S) stereochemistry. Mixtures of isomers of the compounds of Formula I or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns, according to procedures described herein.

Certain of the compounds of the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., amelioration or healing of conditions which respond to modulation of the KCNQ potassium channels. When applied to an individual active ingredient, administered alone, the term refers to that ingredient alone. When applied to a combination, the term refers to combined amounts of the active ingredients that result in the therapeutic effect, whether administered in combination, serially or simultaneously. The term "KCNQ" as used herein and in the claims means the family of KCNQ2, KCNQ3, KCNQ4, and KCNQ5 potassium channel polypeptides as well as heteromultimers of different individual family members which include but are not limited to KCNQ2/3, KCNQ2/5 and KCNQ3/5. The terms "treat, treating, treatment" as used herein and in the claims means preventing, alleviating or ameliorating diseases and/or symptoms associated with dysfunction of cellular membrane polarization and conductance of human KCNQ2, KCNQ3, KCNQ4, and KCNQ5 potassium channel polypeptides and, in particular, migraine and/or symptoms that precede a full-blown migraine attack, neuropathic pain, mania and anxiety.

The general procedures used to synthesize intermediates and the compounds of Formula I are described in Reaction Schemes 1–4 and are illustrated in the preparations and examples. Reasonable variations of the described procedures, which would be evident to one skilled in the art, are intended to be within the scope of the present invention.

Reaction Scheme 1

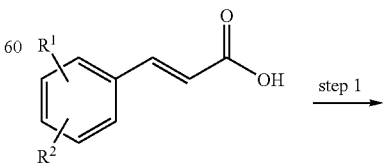

II

-continued

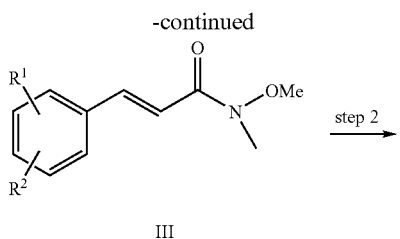

III

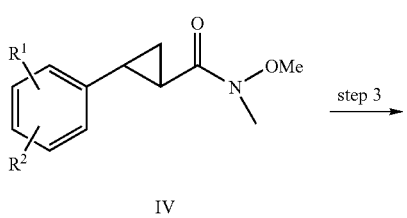

IV

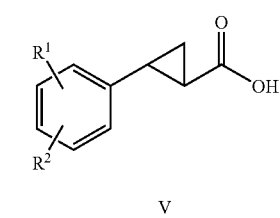

V

Reaction Scheme 1 depicts the preparation of cyclopropanecarboxylic acid derivatives useful as intermediates in the synthesis of compounds of Formula I. Step 1 of Reaction Scheme 1 depicts the reaction of an appropriate cinnamic acid of Formula II with O,N-dimethyl-hydroxylamine hydrochloride and triethylamine to furnish compound of Formula III. Compound of Formula III can be converted to compound of Formula IV by treatment with trimethylsulfoxonium iodide and sodium hydride. Compound of Formula IV can be hydrolyzed under basic conditions such as aqueous sodium hydroxide followed by acidification to give compound of Formula V.

Reaction Scheme 2

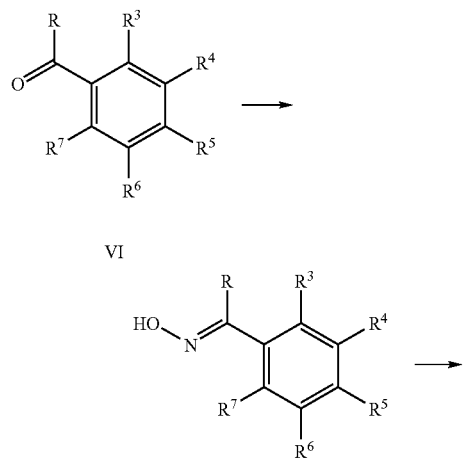

-continued

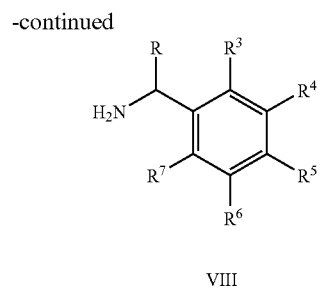

VIII

Reaction Scheme 2 depicts a general method useful for the preparation of amines of Formula VIII which are useful intermediates for the preparation of compounds of Formula I. Compound of Formula VI was converted to compound of Formula VII by reaction with hydroxylamine hydrochloride in the presence of a base such as triethylamine. Compound of Formula VII underwent catalytic hydrogenation to give amine with Formula VIII.

Reaction Scheme 3

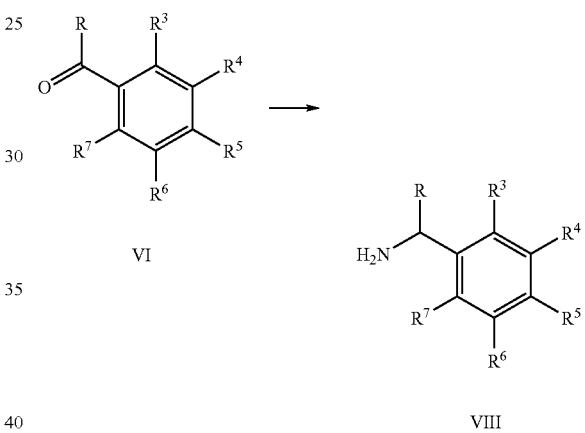

Reaction Scheme 3 depicts an alternative method useful for the preparation of amines of Formula VIII. Compound of Formula VI underwent reductive alkylation with ammonia and a reducing agent such as sodium cyanoborohydride to give compound of Formula VIII.

Reaction Scheme 4

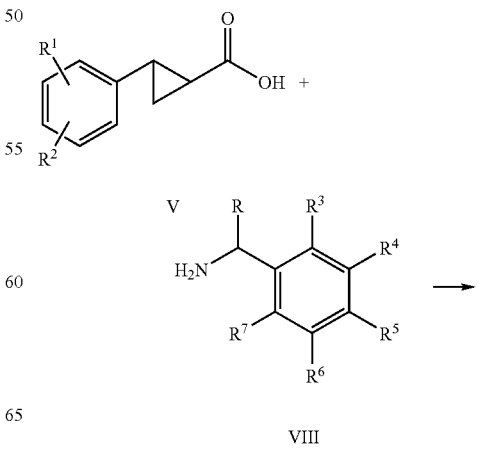

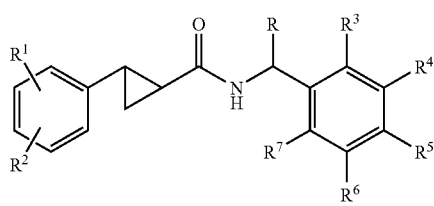

I

Reaction Scheme 4 depicts the preparation of compounds of general Formula I from the acid of general Formula V and amine of Formula VIII. Reaction Scheme 4 depicts the preparation of compounds of general Formula I from the acid of general Formula V and amine of general Formula VIII. The coupling of the acid, V, and amine, VIII is carried out by methodology well known in the art for the conversion of an acid and an amine to form an amide. Useful reactive derivatives of the acid of Formula VIII include, but are not limited to, activated esters, reactive mixed anhydrides, and acid halides (such as the acid chloride, prepared e.g. with thionyl chloride or oxalyl chloride). A preferred method is to condense the acid of Formula V with the amine of Formula III in the presence of an appropriate condensing agent, for example, 1-(3-dimethylaminopropyl)-3-ethylcarbodiimide (EDC) or dicyclohexylcarbodiimide (DCC), and a basic tertiary amine, such as 4-dimethylaminopyridine (DMAP), in an inert solvent such as dichloromethane. The more preferred method is to couple the acid of Formula V with the amine of Formula VIII in the presence of 1-(3-dimethylaminopropyl)-3-ethylcarbodiimide, hydrochloride (EDC) in the presence of 4-dimethylaminopyridine (DMAP), triethylamine ($Et_3N$), in dichloromethane.

In one embodiment, the present invention includes compounds of Formula I or a pharmaceutically acceptable salt thereof

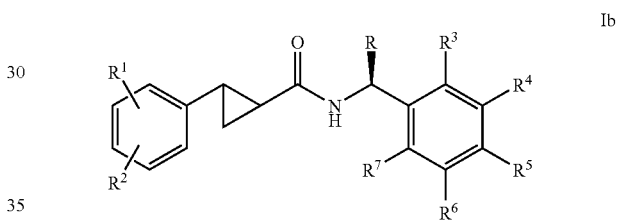

I wherein R is $C_{1-4}$ alkyl, $CF_3$ or hydroxymethyl; $R^1$ and $R^2$ are each independently hydrogen, $C_{1-4}$ alkyl, halogen or morpholin-4-yl; $R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro; $R^5$ is hydrogen or fluoro; or $R^4$ and $R^5$ taken together are —CH=CH—CH=CH— or —$CH_2CH_2O$—; and $R^3$, $R^6$ and $R^7$ are each independently selected from hydrogen or fluoro.

In a preferred embodiment, the invention includes compounds of Formula Ia or a pharmaceutically acceptable salt thereof

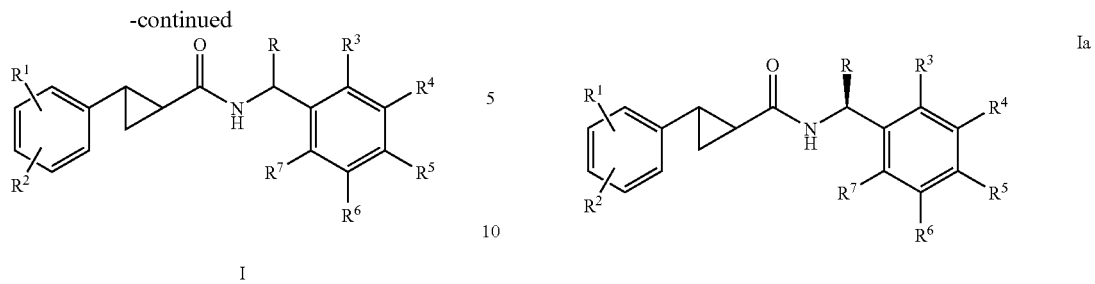

wherein R is methyl; $R^1$ and $R^2$ are each independently hydrogen, $C_{1-4}$ alkyl, halogen or morpholin-4-yl; $R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro; $R^5$ is hydrogen or fluoro; or $R^4$ and $R^5$ taken together are —CH=CH—CH=CH— or —$CH_2CH_2O$—; and $R^3$, $R^6$ and $R^7$ are each independently selected from hydrogen or fluoro.

In a preferred embodiment, the invention includes compounds of Formula Ib or a pharmaceutically acceptable salt thereof Ib wherein R is hydroxymethyl; $R^1$ and $R^2$ are each independently hydrogen, $C_{1-4}$ alkyl, halogen or morpholin-4-yl; $R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro; $R^5$ is hydrogen or fluoro; or $R^4$ and $R^5$ taken together are —CH=CH—CH=CH— or —$CH_2CH_2O$—; and $R^3$, $R^6$ and $R^7$ are each independently selected from hydrogen or fluoro.

Preferred compounds for use in the method of the present invention include the compounds of Formula I listed below:

2-(2-fluoro-phenyl)-cyclopropanecarboxylic acid[1-(2,3-dihydro-benzofuran-5-yl)-ethyl]-amide;

2-(3-fluoro-phenyl)-cyclopropanecarboxylic acid[1-(2,3-dihydro-benzofuran-5-yl)-ethyl]-amide;

2-(4-fluoro-phenyl)-cyclopropanecarboxylic acid[1-(2,3-dihydro-benzofuran-5-yl)-ethyl]-amide;

2-(2-fluoro-phenyl)-cyclopropanecarboxylic acid(2-hydroxy-1-naphthalen-2-yl-ethyl)-amide;

2-(3-fluoro-phenyl)-cyclopropanecarboxylic acid(2-hydroxy-1-naphthalen-2-yl-ethyl)-amide;

2-(4-fluoro-phenyl)-cyclopropanecarboxylic acid(2-hydroxy-1-naphthalen-2-yl-ethyl)-amide;

2-(2,5-difluoro-phenyl)-cyclopropanecarboxylic acid(2-hydroxy-1-naphthalen-2-yl-ethyl)-amide;

2-(2-fluoro-phenyl)-cyclopropanecarboxylic acid[1-(4-fluoro-3-morpholin-4-yl-phenyl)-2-hydroxy-ethyl]-amide;

2-(3-fluoro-phenyl)-cyclopropanecarboxylic acid[1-(4-fluoro-3-morpholin-4-yl-phenyl)-2-hydroxy-ethyl]-amide;
2-(4-fluoro-phenyl)-cyclopropanecarboxylic acid[1-(4-fluoro-3-morpholin-4-yl-phenyl)-2-hydroxy-ethyl]-amide;
2-(2,5-difluoro-phenyl)-cyclopropanecarboxylic acid[1-(4-fluoro-3-morpholin-4-yl-phenyl)-2-hydroxy-ethyl]-amide;
2-(4-fluoro-phenyl)-cyclopropanecarboxylic acid(1-naphthalen-2-yl-ethyl)-amide;
2-(2,5-difluoro-phenyl)-cyclopropanecarboxylic acid(1-naphthalen-2-yl-ethyl)-amide;
2-(4-fluoro-phenyl)-cyclopropanecarboxylic acid{1-[3-(3-dimethylamino-pyrrolidin-1-yl)-phenyl]-ethylI}-amide;
2-(2,5-difluoro-phenyl)-cyclopropanecarboxylic acid{1-[3-(3-dimethylamino-pyrrolidin-1-yl)-phenyl]-ethyl}-amide;
2-(3-fluoro-phenyl)-cyclopropanecarboxylic acid[1-(3-pyridin-3-yl-phenyl)-ethyl]-amide;
2-(2,5-difluoro-phenyl)-cyclopropanecarboxylic acid[1-(3-pyridin-3-yl-phenyl)-ethyl]-amide;
(S)-2-phenyl-cyclopropanecarboxylic acid[1-(3-pyridin-3-yl-phenyl)-ethyl]-amide;
(S)-2-(3-fluoro-phenyl)-cyclopropanecarboxylic acid{1-[3-(6-fluoro-pyridin-3-yl)-phenyl]-ethyl}-amide;
(S)-2-phenyl-cyclopropanecarboxylic acid{1-[3-(2-fluoro-pyridin-3-yl)-phenyl]-ethyl}-amide; and
(S)-2-(2-fluoro-phenyl)-cyclopropanecarboxylic acid{1-[3-(2-fluoro-pyridin-3-yl)-phenyl]-ethyl}-amide;
or a pharmaceutically acceptable salt thereof.

BIOLOGICAL ACTIVITY

KCNQ Patch-Clamp Methods and Results

Potassium (K$^+$) channels are structurally and functionally diverse families of K$^+$-selective channel proteins which are ubiquitous in cells, indicating their central importance in regulating a number of key cell functions [Rudy, B., Neuroscience, 25: 729–749 (1988)]. While widely distributed as a class, K$^+$ channels are differentially distributed as individual members of this class or as families. [Gehlert, D. R., et al., Neuroscience, 52: 191–205 (1993)]. In general, activation of K$^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, K$^+$ channels can respond to important cellular events such as changes in the intracellular concentration of ATP or the intracellular concentration of calcium (Ca$^{2+}$). The central role of K$^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the KCNQ family exemplified by KCNQ2, KCNQ2/3 heteromultimers, and KCNQ5, is regulated by transmembrane voltage and plays a potentially important role in the regulation of neuronal excitability [Biervert, C., et al., Science, 279: 403–406 (1998); Lerche, C. et al., J. Biol. Chem. 275:22395–22400 (2000); Wang, H. et al., Science, 282:1890–1893 (1998)].

An opener of KCNQ channels, such as the KCNQ2 and KCNQ2/3 channel opener retigabine, exerts its cellular effects by increasing the open probability of these channels [Main J., Mol Pharmacol 58(2):253–62 (2000); Wickenden, A. et al., Mol. Pharm. 58:591–600 (2000)]. This increase in the opening of individual KCNQ channels collectively results in the hyperpolarization of cell membranes, particularly in depolarized cells, produced by significant increases in whole-cell KCNQ-mediated conductance.

Whole-cell patch-clamp recordings were made from an HEK 293 stable cell line expressing mKCNQ2 channels, maintained in culture for 1–2 days. Patch pipettes had initial resistances of 2.5–4 MΩ. Currents were recorded with an EPC-9 amplifier (HEKA, Lambrecht, Germany) controlled with software (Pulse, HEKA) run on a standard lab PC. Series resistance compensation was used during current recording, and set at 80%. The series resistance (R) and cell capacitance (C) were determined electronically by subtracting the capacitive currents at the onset and offset of a 5 mV voltage step. The cancellation of whole-cell capacitive transients was virtually complete in all cells. Analog current signals were low-pass filtered at 2.9 kHz using a four-pole Bessel filter –3 dB) and stored on a local network server computer at a sampling rate of 1.5 kHz. All recordings were performed at room temperature (20–22° C.). The pipette solution contained (mM): KCl, 150; CaCl$_2$, 2.5; EGTA, 5; MgCl$_2$, 1; HEPES, 10; pH to 7.3 with KOH, and Osmolality of 290–300 mOsm. The extracellular solution contained (mM): NaCl, 140; KCl, 2.5; CaCl$_2$, 2.5; MgCl$_2$, 1; glucose, 10; HEPES, 10; pH to 7.3 with NaOH, and Osmolality of 305–310 mOsm For analysis of agents effects on mKCNQ2 currents, the raw current records were displayed on the digital oscilloscope of the Pulse software application. Concentration response data were generated by measuring the difference in the steady-state amplitude of current in the presence of compound at the end of a 600 ms voltage-clamp step from a holding potential of –80 mV. The concentration-response data were fitted with Hill-type equations:

$$I = I_{max}/(1 + EC_{50}/[A]^{nH}),$$

where I is the steady-state current at a given concentration of agonist [A]; and $I_{max}$, $EC_{50}$ and nH are parameters estimated from the curve fit. In some cases the concentration-response data were fitted with equations consisting of the sum of two Hill-type components. Current-voltage (I/V) relationships for agonist-evoked currents were obtained by performing 600 ms voltage steps (–110 mV to +40 mV) in the absence and presence of agonist. The effect of a representative compound of Formula I on KCNQ currents is listed in Table 1.

TABLE 1

| Example No. | EC$_{50}$ (µM) @ –40 mv) | I$_{max}$ (%) |
| --- | --- | --- |
| 13 | 0.597 | 1232 |

Thallium Assay Methods and Results

A thallium flux assay was used to detect and characterize openers of KCNQ potassium channels. The thallium assay is generally described in International application WO 02/31508 published Apr. 18, 2002. More specifically, the thallium influx assay to detect compounds that block or open the voltage-gated K$^+$ channel KCNQ2 is described in Example IV of the published WO 02/31508 application.

For data analysis, the amplitude of the average of the negative controls was subtracted from all wells. The amplitudes of the test compounds were then compared to the value of four standard deviations of the negative control wells. The lowest concentration of a test compound sufficient to generate a signal amplitude greater than or equal to four standard deviations from the amplitude of the negative controls was defined as the minimal active concentration.

For generating $EC_{50}$ values, compounds were serially diluted in 1:3 volume increments to produce a 10 point concentration series. $EC_{50}$ values were calculated by fitting the resulting amplitudes to a single-site logistic equation. $EC_{50}$ was defined as the concentration of test compound required to yield 50% of the maximal response. Maximal response (Maximal opening) was the largest signal amplitude above the negative control generated by any concentration of a test compound.

The following Table 2 contains data which show that compounds of the present invention are openers of the KCNQ channels.

TABLE 2

| Example No. | $EC_{50}$ (µM) |
|---|---|
| 9 | 0.022 |
| 11 | 1.44 |
| 13 | 0.012 |
| 14 | 0.001 |
| 15 | 0.001 |
| 32 | 0.001 |
| 34 | 2.21 |

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of KCNQ potassium channels in a mammal in need thereof, which comprises administering to said mammal a therapeutically effective amount of a compound of Formula I. Preferably, the compounds of Formula I are useful in the treatment of treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, plated in a hard gelatin capsule in powder or pellet form, or in the form of a troche or lonzenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 µg/kg to 10 mg/kg body weight. For parenteral administration, the dose may be in the range of 0.1 µg/kg to 1 mg/kg body weight for intravenous administration. For oral administration, the dose may be in the range about 0.1 µg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). ¹H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δTMS=0. The following internal references were used for the residual protons in the following solvents: CDCl₃ ($\delta_H$ 7.26), CD₃OD ($\delta_H$ 3.30) and DMSO-d₆ ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method is as follows unless otherwise noted: Column YMC ODS-A C18 S7 (3.0×50 mm), Start % B=0, Final % B=100, Gradient Time=2 min, Flow rate 5 ml/minutes. Wavelength=220 nm, Solvent A=10% MeOH-90% H₂O-0.1% TFA, Solvent B=90% MeOH—10% H₂O-0.1% TFA; and $R_t$ in min. Preparative reverse phase HPLC was performed on a Shimadzu LC-8A automated preparative HPLC system with detector (SPD-10AV UV-VIS) wavelength and solvent systems (A and B) the same as above except where otherwise noted.

The following LCMS conditions were employed for the analysis of the compounds of Examples 1–36 and are as follows:

a) YMC Xterra C18 S7 3.0×50 mm; 0–100% gradient over 2 min; 5 mL/min flow rate
b) Primeshere C18-HC 4.6×30 mm; (5 mM NH₄OAc) 0–100% gradient over 2 min; 4 mL/min flow rate
c) Xterra C8-HC 4.6×30 mm; (0.05% TFA) 0–100% gradient over 2 min; 4 mL/min flow rate SolventA=10% CH₃CN-90% H₂O-5 mM NH₄OAc SolventB=90% CH₃CN-10% H₂O-5 mM NH₄Oac

PREPARATION OF INTERMEDIATES

Preparation 1

Preparation of 2-(2-chloro-phenyl)-cyclopropanecarboxylic acid

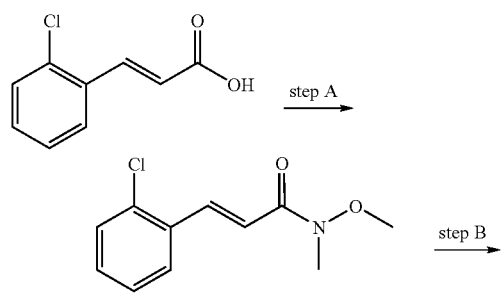

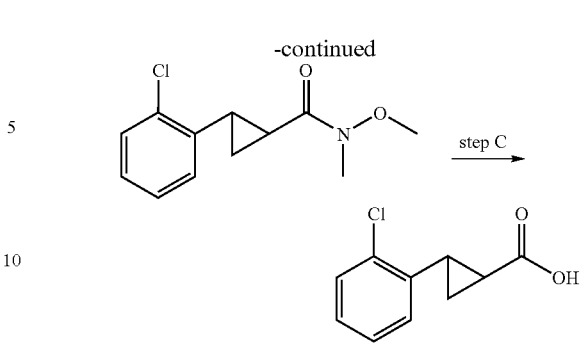

Step A: 3-(2-Chloro-phenyl)-N-methoxy-N-methyl-acrylamide

A mixture of 2-chlorocinnamic acid (18.3 g), EDAC.HCl (23 g), DMAP (12.2 g), triethylamine (28 mL), and NH₂OMe.HCl (12 g) in CH₂Cl₂ (300 mL) was stirred at room temperature for 16 h. The reaction was quenched with water, and the organic layer was washed with brine, dried over MgSO₄ and filtered. The filtrated was evaporated in vacuo, and the crude product was purified by silica gel flash chromatography eluting with 33% hexanes in ethyl acetate gave the title compound (22 g) as a solid.

¹H NMR (300 MHz, CDCl₃) δ 8.13 (d, J=15.8 Hz, 1H), 7.66–7.63 (m, 1H), 7.41–7.38 (m, 1H), 7.28–7.25 (m, 1H), 7.04 (d, J=15.8 Hz, 1H), 3.75 (s, 3H), 3.30 (s, 3H).

MS (M+H)⁺ 226.

Step B: 2-(2-Chloro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(2-chlorophenyl)-N-methoxy-N-methyl-acrylamide (22 g) was added to the above reaction mixture at 0° C., and the resulting reaction was allowed to warm to room temperature and stirred for 2 h. The reaction was quenched with water and the aqueous layer was extracted with CH₂Cl₂. The combined organic layers were washed with brine, dried over MgSO₄, and concentrated in vacuo to give a residue. The residue was purified by flash chromatography over silica gel (elution with 50% hexanes in ethyl acetate) to give the title compound (17 g) as an oil.

¹H NMR (300 MHz, CDCl₃) δ 7.37–7.34 (m, 1H), 7.20–7.15 (m, 1H), 7.08–7.05 (m, 1H), 3.73 (s, 3H), 3.25 (s, 3H). 2.80–2.74 (m, 1H), 2.35–2.29 (m, 1H), 1.67–1.60 (m, 1H), 1.37–1.31 (m, 1H).

MS (M+H)⁺ 240.

Step C: Preparation of 2-(2-chloro-phenyl)-cyclopropanecarboxylic acid

A mixture of 2-(2-chloro-phenyl)-cyclopropanecarboxylic acid methoxy-methyl-amide (9.6 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with CH₂Cl₂. The organic layer was washed with brine, dried over MgSO₄ and concentrated in vacuo to give the title compound (7.8 g).

¹H NMR (300 MHz, CDCl₃) δ 7.39–7.36 (m, 1H), 7.20–7.18 (m, 1H), 7.00–7.01 (m, 1H), 2.85–2.80 (m, 1H), 1.84–1.80 (m, 1H), 1.73–1.66 (m, 1H), 1.46–1.39 (m, 1H).

MS (M−H)⁺ 195.

Preparation 2

Preparation of 2-(3-chloro-phenyl)-cyclopropanecarboxylic acid

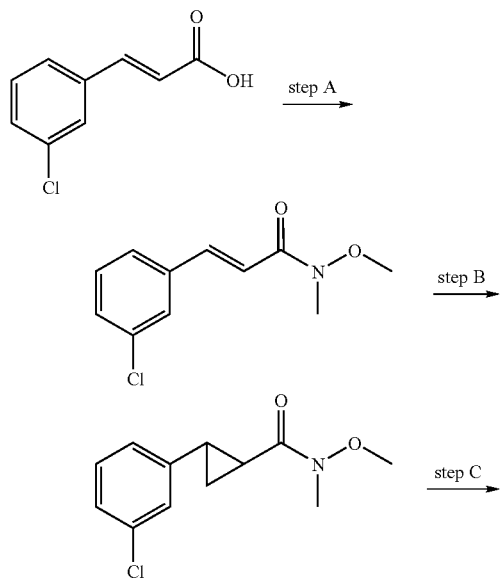

Step A: 3-(3-Chloro-phenyl)-N-methoxy-N-methyl-acrylamide

A mixture of 3-chlorocinnamic acid (18.3 g), EDAC.HCl (23 g), DMAP (12.2 g), triethylamine (28 mL), and NH(Me)OMe.HCl (12 g) in $CH_2Cl_2$ (300 mL) was stirred at room temperature for 16 h. The reaction was quenched with water, and the organic layer was washed with brine, dried over $MgSO_4$ and filtered. The filtrated was evaporated in vacuo, and the crude product was purified by silica gel flash chromatography eluting with 33% hexanes in ethyl acetate gave the title compound (20 g) as a solid.

Step B: 2-(3-Chloro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(3-chloro-phenyl)-N-methoxy-N-methyl-acrylamide (19.5 g) was added to the above reaction mixture at 0° C., and the resulting reaction was allowed to warm to room temperature and stirred for 2 h. The reaction was quenched with water and the aqueous layer was extracted with $CH_2Cl_2$. The combined organic layers were washed with brine, dried over $MgSO_4$, and concentrated in vacuo to give a residue. The residue was purified by flash chromatography over silica gel (elution with 50% hexanes in ethyl acetate) to give the title compound (14 g) as an oil.

$^1$H NMR (300 MHz, $CDCl_3$) δ 7.20–7.01 (m, 3H), 3.70 (s, 3H), 3.23 (s, 3H). 2.48–2.43 (m, 2H), 1.67–1.60 (m, 1H), 1.32–1.25 (m, 1H).

MS $(M+H)^+$ 240.

Step C: Preparation of 2-(2-chloro-phenyl)-cyclopropanecarboxylic acid

A mixture of 2-(3-chloro-phenyl)-cyclopropanecarboxylic acid methoxy-methyl-amide (9.6 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with $CH_2Cl_2$. The organic layer was washed with brine, dried over $MgSO_4$ and concentrated in vacuo to give the title compound (7.4 g).

$^1$H NMR (300 MHz, $CDCl_3$) δ 7.28–7.18 (m, 1H), 7.09 (s, 1H), 7.01–6.99 (m, 1H), 2.58–2.56 (m, 1H), 1.91–1.88 (m, 1H), 1.69–1.65 (m, 1H), 1.41–1.39 (m, 1H).

MS $(M-H)^+$ 195.

Preparation 3

Preparation of 2-(4-chloro-phenyl)-cyclopropanecarboxylic acid

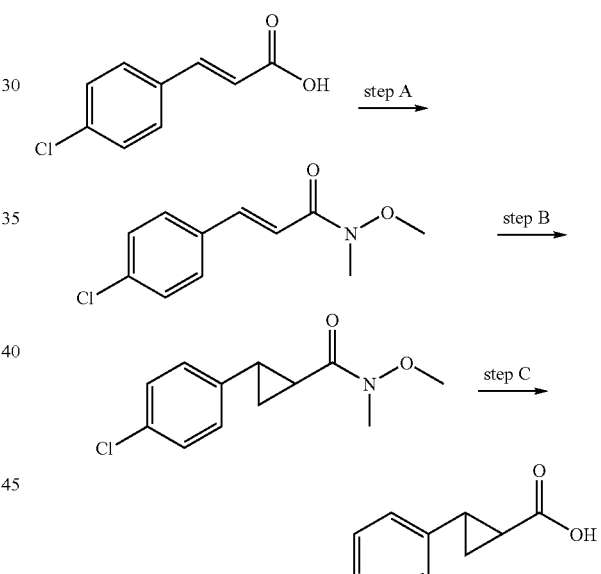

Step A: 3-(4-Chloro-phenyl)-N-methoxy-N-methyl-acrylamide

A mixture of 4-chlorocinnamic acid (18.3 g), EDAC.HCl (23 g), DMAP (12.2 g), triethylamine (28 mL), and $NH_2$OMe.HCl (12 g) in $CH_2Cl_2$ (300 mL) was stirred at room temperature for 16 h. The reaction was quenched with water, and the organic layer was washed with brine, dried over $MgSO_4$ and filtered. The filtrated was evaporated in vacuo, and the crude product was purified by silica gel flash chromatography eluting with 33% hexanes in ethyl acetate gave the title compound (19.5 g) as a solid.

Step B: 2-(4-Chloro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(4-chloro-phenyl)-N-methoxy-N-methyl-acrylamide (19.5 g) was added to the above reaction mixture at 0° C., and the resulting reaction was allowed to warm to room temperature and stirred for 2 h. The reaction was quenched with water and the aqueous layer was extracted with $CH_2Cl_2$. The combined organic layers were washed with brine, dried over $MgSO_4$, and concentrated in vacuo to give a residue. The residue was purified by flash chromatography over silica gel (elution with 50% hexanes in ethyl acetate) to give the title compound (13 g) as an oil.

$^1$H NMR (300 MHz, $CDCl_3$) δ 7.25 (d, J=6.66, 2H), 7.06 (d, J=6.66 Hz, 2H), 3.68 (s, 3H), 3.23 (s, 3H). 2.48–2.38 (m, 2H), 1.65–1.60 (m, 1H), 1.29–1.23 (m, 1H).

MS (M+H)$^+$ 240.

Step C: Preparation of 2-(4-chloro-phenyl)-cyclopropanecarboxylic acid

A mixture of 2-(4-chloro-phenyl)-cyclopropanecarboxylic acid methoxy-methyl-amide (9.6 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with $CH_2Cl_2$. The organic layer was washed with brine, dried over $MgSO_4$ and concentrated in vacuo to give the title compound (7.3 g).

$^1$H NMR (300 MHz, $CDCl_3$) δ 7.27 (d, J=10 Hz, 2H), 7.05 (d, J=10 Hz, 2H), 2.58–2.56 (m, 1H), 1.87–1.85 (m, 1H), 1.68–1.65 (m, 1H), 1.39–1.36 (m, 1H),

MS (M−H)$^+$ 195.

Preparation 4

Preparation of 2-(2-fluoro-phenyl)-cyclopropanecarboxylic acid

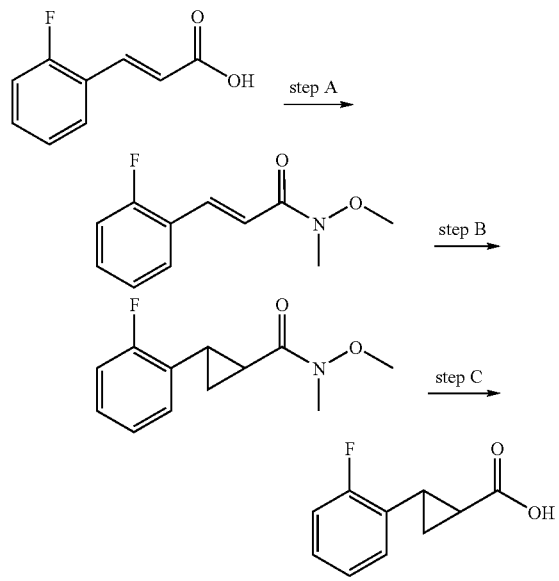

Step A: 3-(2-Fluoro-phenyl)-N-methoxy-N-methyl-acrylamide

A mixture of 2-fluorocinnamic acid (16.6 g), EDAC.HCl (23 g), DMAP (12.2 g), triethylamine (28 mL), and $NH_2OMe \cdot HCl$ (12 g) in $CH_2Cl_2$ (300 mL) was stirred at room temperature for 16 h. The reaction was quenched with water, and the organic layer was washed with brine, dried over $MgSO_4$ and filtered. The filtrated was evaporated in vacuo, and the crude product was purified by silica gel flash chromatography eluting with 33% hexanes in ethyl acetate gave the title compound (20 g) as a solid.

$^1$H NMR (300 MHz, $CDCl_3$) δ 7.84 (d, J=16.0 Hz, 1H), 7.56–7.53 (m, 1H), 7.34–7.31 (m, 1H), 7.17–7.05 (m, 2H), 3.76 (s, 3H), 3.31 (s, 3H).

MS (M+H)$^+$ 210.

Step B: 2-(2-Fluoro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(2-fluoro-phenyl)-N-methoxy-N-methyl-acrylamide (19.5 g) was added to the above reaction mixture at 0° C., and the resulting reaction was allowed to warm to room temperature and stirred for 2 h. The reaction was quenched with water and the aqueous layer was extracted with $CH_2Cl_2$. The combined organic layers were washed with brine, dried over $MgSO_4$, and concentrated in vacuo to give a residue. The residue was purified by flash chromatography over silica gel (elution with 50% hexanes in ethyl acetate) to give the title compound (16 g) as an oil.

$^1$H NMR (300 MHz, $CDCl_3$) δ 7.13–7.08 (m, 1H), 7.01–6.92 (m, 2H), 3.66 (s, 3H), 3.19 (s, 3H). 2.58–2.54 (m, 1H), 2.40–2.35 (m, 1H), 1.60–1.54 (m, 1H), 1.32–1.25 (m, 1H).

MS (M+H)$^+$ 224.

Step C: Preparation of 2-(2-fluoro-phenyl)-cyclopropanecarboxylic acid

A mixture of 2-(2-fluoro-phenyl)-cyclopropanecarboxylic acid methoxy-methyl-amide (8.92 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with $CH_2Cl_2$. The organic layer was washed with brine, dried over $MgSO_4$ and concentrated in vacuo to give the title compound (7 g).

$^1$H NMR (300 MHz, $CDCl_3$) δ 7.26–7.18 (m, 1H), 7.08–6.95 (m, 2H), 2.75–2.71 (m, 1H), 1.95–1.91 (m, 1H), 1.70–1.63 (m, 1H), 1.49–1.43 (m, 1H).

Preparation 5

Preparation of 2-(3-fluoro-phenyl)-cyclopropanecarboxylic acid

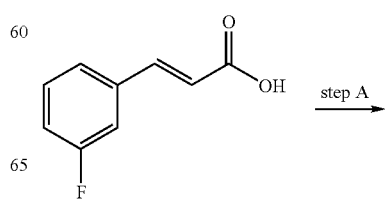

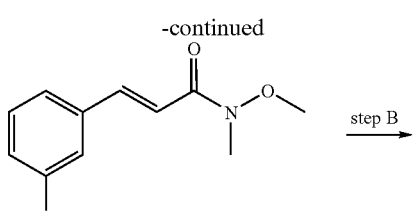

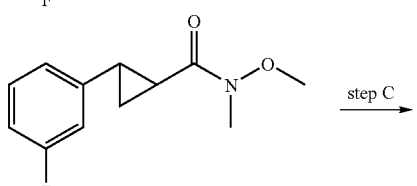

Step A: 3-(3-Fluoro-phenyl)-N-methoxy-N-methyl-acrylamide

A mixture of 3-fluorocinnamic acid (16.6 g), EDAC.HCl (23 g), DMAP (12.2 g), triethylamine (28 mL), and NH₂OMe.HCl (12 g) in CH₂Cl₂ (300 mL) was stirred at room temperature for 16 h. The reaction was quenched with water, and the organic layer was washed with brine, dried over MgSO₄ and filtered. The filtrated was evaporated in vacuo, and the crude product was purified by silica gel flash chromatography eluting with 33% hexanes in ethyl acetate gave the title compound (20.2 g) as a solid.

$^1$H NMR (300 MHz, CDCl$_3$) δ 7.70 (d, J=15.81 Hz, 1H), 7.36–7.23 (m, 3H), 7.08–6.99 (m, 2H), 3.77 (s, 3H), 3.31 (s, 3H).

MS (M+H)$^+$ 210.

Step B: 2-(3-Fluoro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(3-fluoro-phenyl)-N-methoxy-N-methyl-acrylamide (20 g) was added to the above reaction mixture at 0° C., and the resulting reaction was allowed to warm to room temperature and stirred for 2 h. The reaction was quenched with water and the aqueous layer was extracted with CH₂Cl₂. The combined organic layers were washed with brine, dried over MgSO₄, and concentrated in vacuo to give a residue. The residue was purified by flash chromatography over silica gel (elution with 50% hexanes in ethyl acetate) to give the title compound (18 g) as an oil.

$^1$H NMR (300 MHz, CDCl$_3$) δ 7.25–7.18 (m, 1H), 6.93–6.78 (m, 2H), 3.69 (s, 3H), 3.23 (s, 3H). 2.53–2.44 (m, 2H), 1.67–1.60 (m, 1H), 1.30–1.25 (m, 1H). MS (M+H)$^+$ 224.

Step C: Preparation of 2-(3-fluoro-phenyl)-cyclopropanecarboxylic acid

A mixture of 2-(3-fluoro-phenyl)-cyclopropanecarboxylic acid methoxy-methyl-amide (8.96 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with CH₂Cl₂. The organic layer was washed with brine, dried over MgSO₄ and concentrated in vacuo to give the title compound (7.1 g).

$^1$H NMR (300 MHz, CDCl$_3$) δ 7.28–7.21 (m, 1H), 7.94–6.88 (m, 2H), 6.81–6.76 (m, 1H), 2.60–2.57 (m, 1H), 1.92–1.87 (m, 1H), 1.71–1.66 (m, 1H), 1.42–1.37 (m, 1H).

MS (M–H)$^+$ 179.

Preparation 6

Preparation of 2-(4-fluoro-phenyl)-cyclopropanecarboxylic acid

Step A: 3-(4-Fluoro-phenyl)-N-methoxy-N-methyl-acrylamide

A mixture of 4-fluorocinnamic acid (16.6 g), EDAC.HCl (23 g), DMAP (12.2 g), triethylamine (28 mL), and NH₂OMe.HCl (12 g) in CH₂Cl₂ (300 mL) was stirred at room temperature for 16 h. The reaction was quenched with water, and the organic layer was washed with brine, dried over MgSO₄ and filtered. The filtrated was evaporated in vacuo, and the crude product was purified by silica gel flash chromatography eluting with 33% hexanes in ethyl acetate gave the title compound (20.5 g) as a solid.

$^1$H NMR (300 MHz, CDCl$_3$) δ 7.71 (d, J=15.71 Hz, 1H), 7.56–7.53 (m, 2H), 7.08–7.03 (m, 1H), 6.92 (d, J=15.71 Hz, 1H), 3.75 (s, 3H), 3.30 (s, 3H).

MS (M+H)$^+$ 210.

Step B: 2-(4-Fluoro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(4-fluoro-phenyl)-N-methoxy-N-methyl-acrylamide (20.4 g) was added to the above reaction mixture at 0° C., and the resulting reaction was allowed to warm to room temperature and stirred for 2 h. The reaction was quenched with water and the aqueous layer was extracted with $CH_2Cl_2$. The combined organic layers were washed with brine, dried over $MgSO_4$, and concentrated in vacuo to give a residue. The residue was purified by flash chromatography over silica gel (elution with 50% hexanes in ethyl acetate) to give the title compound (15 g) as an oil.

$^1$H NMR (300 MHz, $CDCl_3$) δ 7.11–6.93 (m, 4H), 3.69 (s, 3H), 3.23 (s, 3H). 2.53–2.44 (m, 2H), 1.64–1.57 (m, 1H), 1.27–1.25 (m, 1H).

MS (M+H)$^+$ 224.

Step C: Preparation of 2-(4-fluoro-phenyl)-cyclopropanecarboxylic acid

A mixture of 2-(3-fluoro-phenyl)-cyclopropanecarboxylic acid methoxy-methyl-amide (8.96 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with $CH_2Cl_2$. The organic layer was washed with brine, dried over $MgSO_4$ and concentrated in vacuo to give the title compound (7.1 g).

$^1$H NMR (300 MHz, $CDCl_3$) δ 7.10–6.94 (m, 4H), 2.60–2.57 (m, 1H), 1.87–1.82 (m, 1H), 1.69–1.64 (m, 1H), 1.40–1.35 (m, 1H).

Preparation 7

Preparation of 2-(2,5-difluoro-phenyl)-cyclopropanecarboxylic acid

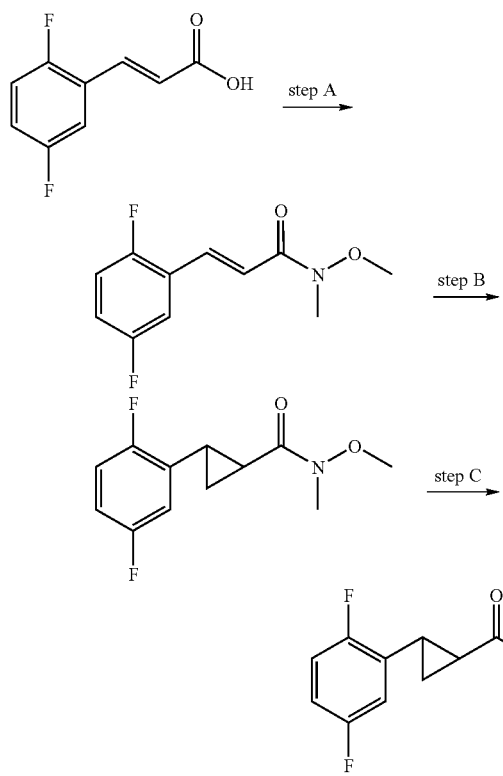

Step A: 3-(2,5Difluoro-phenyl)-N-methoxy-N-methyl-acrylamide

A mixture of 2,5-difluorocinnamic acid (18.4 g), EDAC.HCl (23 g), DMAP (12.2 g), triethylamine (28 mL), and $NH_2OMe.HCl$ (12 g) in $CH_2Cl_2$ (300 mL) was stirred at room temperature for 16 h. The reaction was quenched with water, and the organic layer was washed with brine, dried over $MgSO_4$ and filtered. The filtrated was evaporated in vacuo, and the crude product was purified by silica gel flash chromatography eluting with 33% hexanes in ethyl acetate gave the title compound (22.1 g) as a solid.

$^1$H NMR (300 MHz, $CDCl_3$) δ 7.79 (d, J=15.96 Hz, 1H), 7.27–7.22 (m, 1H), 7.05–6.99 (m, 3H), 3.79 (s, 3H), 3.30 (s, 3H).

MS (M+H)$^+$ 228.

Step B: 2-(2,5difluoro-phenyl)-cyclopropanecarboxylic acid methoxy-methyl-amide

NaH (8 g, 60% oil dispersion) was added to a suspension of trimethylsulfoxonium iodide (44 g) in DMF (150 mL) at 0° C. The resulting mixture was allowed to warm to room temperature and stirred for 0.5 h. A solution of 3-(2,5-difluoro-phenyl)-N-methoxy-N-methyl-acrylamide (21 g) was added to the above reaction mixture at 0° C., and the resulting reaction was allowed to warm to room temperature and stirred for 2 h. The reaction was quenched with water and the aqueous layer was extracted with $CH_2Cl_2$. The combined organic layers were washed with brine, dried over $MgSO_4$, and concentrated in vacuo to give a residue. The residue was purified by flash chromatography over silica gel (elution with 50% hexanes in ethyl acetate) to give the title compound (18 g) as an oil.

$^1$H NMR (300 MHz, $CDCl_3$) δ 6.96–6.93 (m, 1H), 6.86–6.82 (m, 1H), 6.72–6.67 (m, 1H), 3.71 (s, 3H), 3.24 (s, 3H). 2.69–2.60 (m, 1H), 2.38–2.42 (m, 1H), 1.670–1.60 (m, 1H), 1.1.31–1.26 (m, 1H).

MS (M+H)$^+$ 242.

Step C: Preparation of 2-(2,5-difluoro-phenyl)-cyclopropanecarboxylic acid

A mixture of 2-(2,5-difluoro-phenyl)-cyclopropanecarboxylic acid methoxy-methyl-amide (9.6 g), water (20 mL), and NaOH (3.2 g) in MeOH (40 mL) was refluxed for 3 h. The reaction mixture was cooled down to room temperature and concentrated in vacuo. The residue was acidified by 6 N HCl followed by extraction with $CH_2Cl_2$. The organic layer was washed with brine, dried over $MgSO_4$ and concentrated in vacuo to give the title compound (7.8 g).

$^1$H NMR (300 MHz, $CDCl_3$) δ 7.02–6.86 (m, 2H), 6.68–6.62 (m, 1H), 2.74–2.68 (m, 1H), 1.94–1.89 (m, 1H), 1.71–1.67 (m, 1H), 1.44–1.39 (m, 1H).

Preparation 8

Preparation of {1-[3-(1-Amino-ethyl)-phenyl]-pyrrolidin-3-yl}-dimethyl-amine

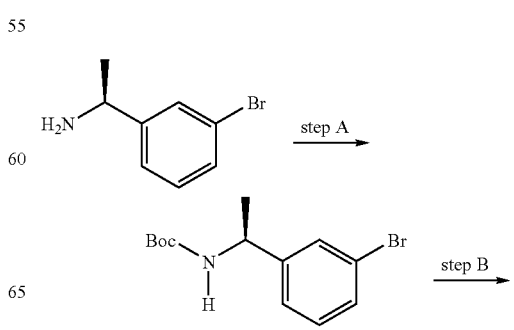

-continued

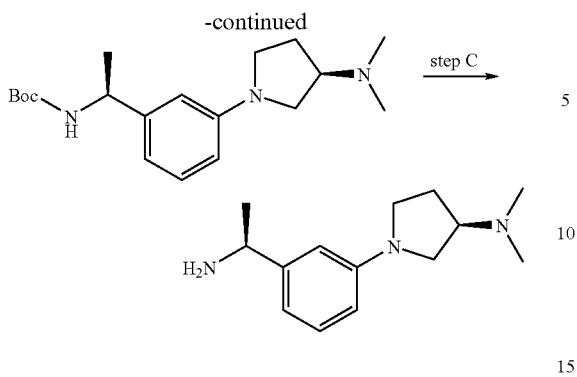

Step A: [(S)-1-(3-Bromo-phenyl)-ethyl]-carbamic acid tert-butyl ester

To a solution of (S)-1-(3-bromo-phenyl)-ethylamine (8 g, 40 mmol) and Et$_3$N (8.4 mL, 60 mmol) in CH$_2$Cl$_2$ (200 mL) was added di-tert-butyl dicarbonate (8.7 g, 40 mmol), and the reaction mixture was stirred at room temperature for 4 h. HCl 0.25 N (100 mL) was added and the two layers were separated. The organic layer was dried over anhydrous magnesium sulfate and filtered, and the filtrate was concentrated in vacuo to provide the title compound (12 g) as a white solid.

$^1$H NMR (CDCl$_3$, 400 MHz): δ 1.42 (m, 12H), 4.76 (m, 3H), 7.1–7.3 (m, 2H), 7.36 (d, J=7.1 Hz, 1H). 7.46 (s, 1H).

Step B: {1-[3-(3-Dimethylamino-pyrrolidin-1-yl)-phenyl]-ethyl}-carbamic acid tert-butyl ester A mixture of (S )[1-(3-bromo-phenyl)-ethyl]-carbamic acid tert-butyl ester (6 g), (3R)-3-(dimethylamino)-pyrrolidine (4.56 g), Pd$_2$(dba)$_3$ (1.83 g), di-t-butyl-biphenylphosphine (600 mg), K$_3$PO$_4$ (8.48 g) in DME (40 mL) was stirred at reflux for 16 h. The reaction mixture was cooled down to room temperature, diluted with methylene chloride, and filtered. The filtrated was evaporated in vacuo, and the crude product was purified by Flash Chromatography using Biotage eluting with 20% MeOH in ethyl acetate to give the title compound (1.8 g) as an oil.

MS (M+H)$^+$ 334.

Step C: 1-[3-(1-Amino-ethyl)-phenyl]-pyrrolidin-3-yl}-dimethyl-amine

A mixture of {1-[3-(3-dimethylamino-pyrrolidin-1-yl)-phenyl]-ethyl}-carbamic acid tert-butyl ester (1.8 g) and 4 ml of 4 N HCl in ethyl acetate (10 mL) at 50° C. was stirred for 2 h. After concentration, the residue was neutralized with 10 N NaOH and extracted with methylene chloride. The organic layer was washed with brine, dried over Na$_2$SO$_4$, and concentrated to give the crude product (1.25 g) as an oil.

MS (M+H)$^+$ 234.

Preparation 9

Preparation of (R)-2-Amino-2-(4-fluoro-3-morpholin-4-yl-phenyl)-ethanol

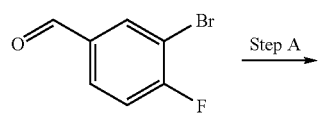

-continued

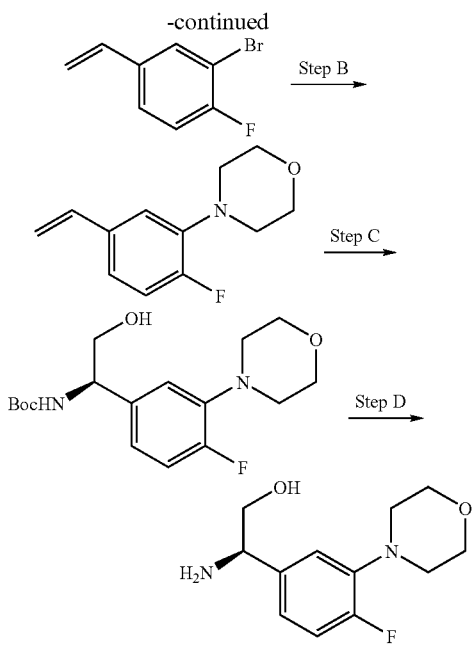

Step A: 2-Bromo-1-fluoro-4-vinyl-benzene

To a suspension of Ph$_3$PCH$_3$Br (57 g) in THF (240 mL) at 0° C. was dropwise added n-BuLi (1.6 N, 100 mL). The resulting mixture was allowed to warm to room temperature and stirred for 1 h. After recooling to 0° C., a solution of 3-bromo-4-fluoro-benzaldehyde (20.3 g) in THF (20 mL) was added. The resulting mixture was allowed to warm to room temperature and stirred for 1 h. The reaction mixture was quenched with water, concentrated, and extracted with methylene chloride. The combined organic layers were dried over magnesium sulfate, concentrated under vacuum. The crude product was purified by flash chromatography eluting with 10% ethyl acetate in hexanes to give the title compound as an oil (18 g).

$^1$H NMR (CDCl$_3$): δ 7.59–7.56 (m, 1H), 7.31–7.27 (m, 1H), 7.05 (t, J=8.4 Hz, 1H), 6.65 (dd, J=17.7, 11.1 Hz, 1H), 6.55 (d, J=17.4 Hz, 1H), 5.28 (d, J=10.8 Hz, 1H).

Step B: 4-(2-Fluoro-5-vinyl-phenyl)-morpholine

A mixture of 2-bromo-1-fluoro-4-vinyl-benzene (8 g), morpholine (20 mL), Pd$_2$(dba)$_2$ (1.83 g), di-t-butyl-biphenylphosphine (1.2 g), K$_3$PO$_4$ (17 g) in DME (60 mL) was stirred at reflux for 4 h. The reaction mixture was cooled down to room temperature, diluted with methylene chloride, and filtered. The filtrate was concentrated in vacuo. The crude product was purified by Flash Chromatography of Biotage eluting with 7% ethyl acetate in hexanes to give the title compound as an oil (5 g).

$^1$H NMR (CDCl$_3$): δ 7.24–6.93 (m, 3H), 6.68 (dd, J=17.7, 10.8 Hz, 1H), 5.66 (d, J=17.4 Hz, 1H), 5.22 (d, J=10.8 Hz, 1H). 3.88 (m, 4H), 3.10 (m, 4H).

MS (M+H)$^+$ 208.

Step C: (R )-4-of [1-(Fluoro-3-morpholin-4-yl-phenyl)-2-hydroxy-ethyl]-carbamic acid tert-butyl ester Sodium hydroxide (3.6 g) was dissolved in water (220 mL). 10 mL of this solution was used to dissolve potassium osmium (VI) oxide dihydrate (434 mg) to get a purple suspension. The rest of the sodium hydroxide solution was treated with t-butyl carbamate (10.666 g) in n-propanol (120 mL), followed by addition of t-butyl hypochlorite (11 mL). This solution was stirred for 5 min, then (DHQD)$_2$PHAL (1466 mg) in n-propanol (120 mL) was added, followed by a solution of 4-(2-Fluoro-5-vinyl-phenyl)-morpholine (5 g) in n-propanol (206 mL) and a solution of potassium osmium (VI) oxide dihydrate previously made. The reaction mixture was stirred at room temperature for 0.5 h. The reaction mixture was quenched with saturated Na$_2$SO$_3$ solution. After concentration, the residue was extracted with ethyl acetate. The combined organic layers were dried over magnesium sulfate, concentrated under vacuum. The crude product was purified by flash chromatography eluting with 33% ethyl acetate in hexanes to give the title compound as a solid (2.2 g).

$^1$H NMR (CDCl$_3$): δ 7.03–6.83 (m,3H), 5.19 (br s, 1HO, 4.68 (br s, 1H), 3.87 (m, 6H), 3.09 (m, 4H), 1.44 (s, 9H).

MS (M+H)$^+$ 341.

Step D: (R)-2-Amino-2-(4-fluoro-3-morpholin-4-yl-phenyl)-ethanol

A solution of TFA (5 mL) and (R )-[1-(fluoro-3-morpholin-4-yl-phenyl)-2-hydroxy-ethyl]-carbamic acid tert-butyl ester(1.2 g) in methylene chloride (15 mL) was stirred for 2 h. After concentration, the residue was neutralized with 10 N NaOH and extracted with methylene chloride. The organic layer was washed with brine, dried over Na$_2$SO$_4$, and concentrated in vacuo to give the title compound as a solid (720 mg).

$^1$H NMR (CDCl$_3$): δ 7.07–6.87 (m, 3H), 4.04–4.00 (m, 1H), 3.87–3.84 (m, 4H), 3.73–3.68 (m, 1H), 3.55–3.52 (m, 1H), 3.09–3.06 (m, 4H).

MS (M+H)$^+$ 241.

Preparation 10

Preparation of (R)-2-Amino-2-naphthalen-2-yl-ethanol hydrochloride

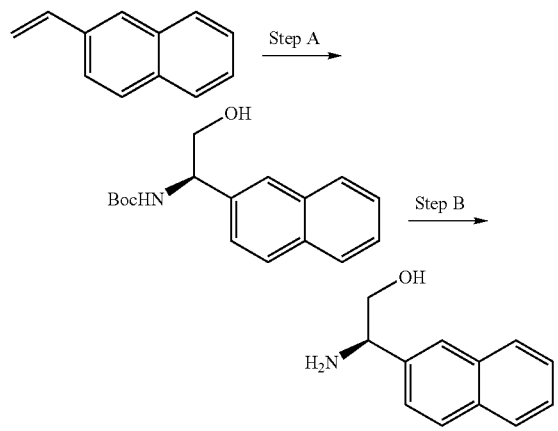

Step A: (R)-(2-Hydroxy-1-naphthalen-2-yl-ethyl)-carbamic acid tert-butyl ester

Sodium hydroxide (1.89 g, 16 mmol) was dissolved in water (115 mL). 5.4 mL of this solution was used to dissolve potassium osmium (VI) oxide dihydrate (240 mg) to get a purple suspension. The rest of the sodium hydroxide solution was treated with t-butyl carbamate (5.580 g, 47.1 mmol) in n-propanol (54 mL), followed by addition of t-butyl hypochlorite (5.4 mL, 47.1 mmol). This solution was stirred for 5 min, then (DHQD)$_2$PHAL (630 mg) in n-propanol (54 mL) was added, followed by a solution of 2-vinylnaphthalene (2.5 g, 16 mmol) in n-propanol (54 mL) and a solution of potassium osmium (VI) oxide dihydrate previously made. The reaction mixture was stirred at room temperature for 0.5 hr. The reaction mixture was quenched with saturated NaHSO$_3$ solution. After concentration, the residue was extracted with ethyl acetate. The combined organic layer was dried over magnesium sulfate, concentrated under vacuum. The crude product was purified by flash chromatography with 20% ethyl acetate in hekanes to give the title compound (2.6 g) as a solid.

$^1$H NMR (CDCl$_3$): δ 7.83–7.74 (m, 4H), 7.47–7.37 (m, 3H), 5.39 (br s, 1H), 4.91 (br s, 1H), 3.90 (d, J=3.9 Hz, 2H), 1.44 (s, 9H).

MS (M+H)$^+$ 288.

Step B: (R)-2-Amino-2-naphthalen-2-yl-ethanol hydrochloride (R)-(2-Hydroxy-1-naphthalen-2-yl-ethyl)-carbamic acid tert-butyl ester (2.5 g) and 9 mL of 4 N HCl in ethyl acetate at 50° C. was stirred for 2 h. After concentration, the residue was neutralized with 10 N NaOH and extracted with methylene chloride. The organic layer was washed with brine, dried over Na$_2$SO$_4$, and concentrated to give the title compound (1.2 g) as a solid which was used in the next step without further purification.

MS (M+H)$^+$ 188.

Preparation 11

Preparation of (S)-1-(3-pyridin-3-yl-phenyl)-ethylamine

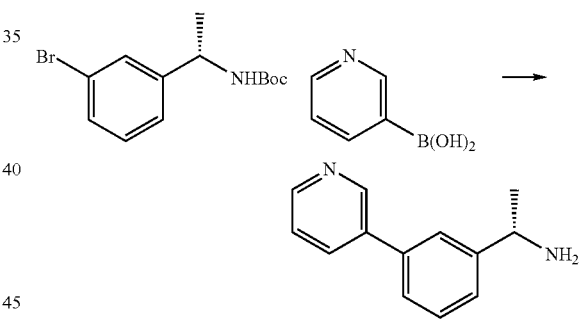

To a solution of (S)-1-(3-bromo-phenyl)-ethyl]-carbamic acid tert-butyl ester (1.5 g, 5 mmol) and pyridine-3-boronic acid (921 mg, 7.5 mmol) in ethyleneglycoldimethylether (25 mL) in a sealed tube were added cesium carbonate (3.25 g, 10 mmol) and water (10 mL). Argon was bubbled into the above mixture for 10 min, and Pd(PPh$_3$)$_4$ (289 mg, 0.25 mmol) was added. The reaction mixture was stirred at 100° C. for 18 h and cooled down to room temperature. Ethyl acetate (100 mL) was added, the resulting solution was washed with NH$_4$Cl (sat.) (2×100 mL), the organic layer was dried over anhydrous magnesium sulfate, filtered and the filtrate was concentrated in vacuo. The crude product was diluted in CH$_2$Cl$_2$ (30 mL) and trifluoroacetic acid (10 mL). The reaction mixture was agitated for 1 h and concentrated in vacuo. The residue was purified by solid phase extraction (SCX cartridge, silca gel benzene sulfonic acid linked) to give the title product (424 mg) as a yellow oil.

$^1$H NMR (CDCl$_3$, 400 MHz): δ 1.26 (d, 3H, J=6.6 Hz), 3.90 (q, 1H, J=6.6 Hz), 6.87 (dd, 1H, J=4.8, 7.8 Hz), 7.2–7.35 (m, 3H), 7.45–7.55 (m, 2H), 8.64 (s, 1H),9.11 (s, 1H).

Preparation 12

Preparation of (S)-1-[3-(6-Chloro-pyridin-3-yl)-phenyl]-ethylamine

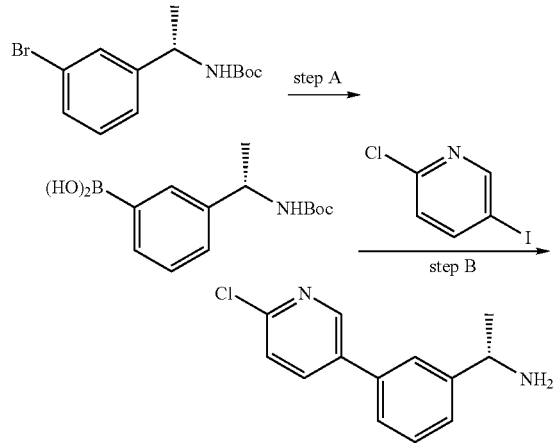

Step A: [(S)-1-(phenyl 3-Boronic acid)-ethyl]-carbamic acid tert-butyl ester (S)-1-(3-Bromo-phenyl)-ethyl]-carbamic acid tert-butyl ester (5 g, 16.6 mmol) were added in THF (100 mL)and cooled to −78° C., methyllithium (11.8 mL, 1.4M in Et₂O, 16.6 mmol) was added, and the reaction mixture was stirred for 5 min. tert-Butyllithium (19.6 mL, 1.7 M in pentane, 33.4 mmol) was added, the reaction mixture was stirred for 5 min, and trimethylborate (2.82 mL, 24.9 mmol) was added rapidly. The reaction mixture was agitated for 1 h, NH₄Cl (sat.) (100 mL) was added, and the resulting solution was allowed to reach 23° C. The reaction mixture was extracted with ethyl acetate (3×100 mL), the organic layer was dried over anhydrous magnesium sulfate and filtered, and the filtrate was concentrated in vacuo. The crude product was purified by flash chromatography (30% EtOAC/Hex.) to provide the title compound (2.7 g) as white solid.

$^1$H NMR (DMSO d₆, 400 MHz): δ 1.2–1.4 (m, 12H), 4.6–4.7 (m, 3H), 7.2–7.4 (m, 2H), 7.6–7.8 (m, 2H).

Step B: (S)-1-[3-(6-chloro-pyridin-3-yl)-phenyl]-ethylamine

To a solution of (S)-1-(phenyl-3-boronic acid)-ethyl]-carbamic acid tert-butyl ester (1.29 g, 4.86 mmol) and 2-chloro-5-Iodo-pyridine (1.4 g, 11.4 mmol) in ethyleneglycoldimethylether (25 mL) in a sealed tube were added cesium carbonate (4.75 g, 14.6 mmol) and water (5 mL). Argon was bubbled in to the above mixture for 10 min, and Pd(PPh₃)₄ (280 mg, 0.24 mmol) was added. The reaction mixture was stirred at 100° C. for 18 h and then cooled down to room temperature. Ethyl acetate (100 mL) was added, the resulting solution was washed with NH₄Cl (sat.) (2×100 mL), and the organic layer was dried over anhydrous magnesium sulfate and filtered. The filtrate was concentrated in vacuo and the crude product was diluted in CH₂Cl₂ (30 mL) and trifluoroacetic acid (10 mL). The reaction mixture was agitated for 1 h and concentrated in vacuo. The residue was purified by solid phase extraction (SCX cartridge, silca gel benzene sulfonic acid linked) to give the title product (785 mg, 69%) as yellow oil.

$^1$H NMR (DMSO d₆, 400 MHz): δ 1.28 (d, 3H, J=6.8 Hz), 4.04 (q, 1H, J=6.8 Hz), 7.4–7.45 (m, 2H), 7.5–7.55 (m, 1H), 7.61 (d, 1H J =7.8 Hz,), 7.72 (s, 1H), 8.15 (dd, 1H, J=8.3, 2.5 Hz,), 8.73 (d, 1H, J=3.3 Hz).

Preparation 13

Preparation of (S)-1-[3-(6-fluoro-pyridin-3-yl)-phenyl]-ethylamine

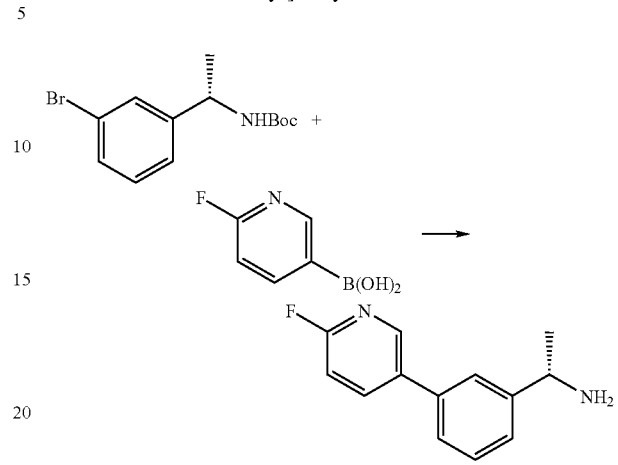

To a solution of (s)-1-(3-Bromo-phenyl)-ethyl]-carbamic acid tert-butyl ester (2.3 g, 7.6 mmol) and 2-fluoropyridine-3-boronic acid (1 g, 7.09 mmol in ethyleneglycoldimethylether (30 mL) were added cesium carbonate (6.3 g, 19.3 mmol) and water (5 mL. Argon was bubbled into the above solution for 10 min, and Pd(PPh₃)₄ (372 mg, 0.32 mmol) was added. The reaction mixture was stirred at 100° C. for 18 h and then cooled down to room temperature. Ethyl acetate (100 mL) was added, the resulting solution was washed with NH₄Cl (sat.) (2×100 mL), and the organic layer was dried over anhydrous magnesium sulfate and filtered. The filtrate was concentrated in vacuo and the crude product was diluted in CH₂Cl₂ (30 mL) and trifluoroacetic acid (10 mL). The reaction mixture was agitated for 1 h and concentrated in vacuo. The residue was purified by solid phase extraction (SCX cartridge, silca gel benzene sulfonic acid linked) to give the title product (1.18 g) as brown oil.

$^1$H NMR (DMSO d₆, 400 MHz): δ 1.26 (d, 3H, J=6.6 Hz), 4.06 (q, 1H, J=6.6 Hz), 7.28 (dd, 1H J=8.6, 3.3 Hz,), 7.4–7.45 (m, 2H), 7.5–7.55 (m, 1H), 7.71 (s, 1H), 8.27 (dd, 1H J=8.6, 2.8 Hz,), 8.54 (d, 1H J=2.5 Hz,).

EXAMPLES

Example 1

2-(4-chloro-phenyl)-cyclopropanecarboxylic acid[1-(2,3-dihydro-benzofuran-5-yl)-ethyl]-amide

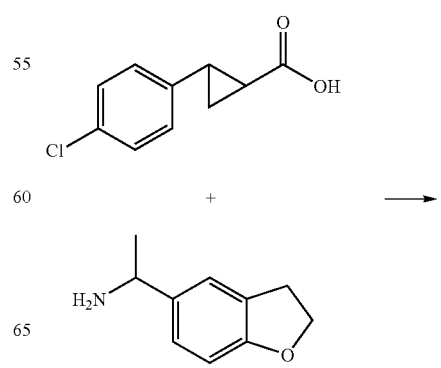

-continued

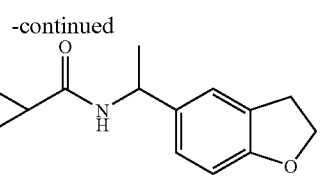

A mixture of 1-(2,3-dihydro-benzofuran-5-yl)-ethylamine (0.1 mmol), 2-(4-Chloro-phenyl)-cyclopropanecarboxylic acid (0.1 mmol), EDAC.HCl (0.2 mmol), DMAP (0.2 mmol), and triethylamine (0.4 mmol) in dichloromethane (2 mL) was stirred at room temperature overnight. The reaction mixture was purified by flash chromatography eluting with 50% hexanes in ethyl acetate to give the title compound (23 mg) as a solid.

$^1$H NMR (CDCl$_3$): δ 7.24–7.16 (m, 3H), 7.07–6.96 (m, 3H), 6.75–6.71 (m, 1H), 5.09–5.04 (m, 1H), 4.59–4.53 (m, 2H), 3.22–3.15 (m, 2H), 2.47–2.43 (m, 1H), 1.63–1.46 (m, 5H), 1.19–1.15 (m, 1H).

MS (M+H)$^+$ 342.

HPLC rt: 1.46 min (method a)

Examples 2–7

Examples 2–7 were prepared from appropriate acids by the general procedure used to prepare Example 1.

| Example No. | Structure | Chemical Name | HPLC rt (min), method | Mass (M + H)$^+$ m/z |
|---|---|---|---|---|
| 2 | 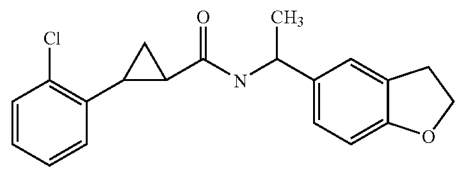 | 2-(2-Chloro-phenyl)-cyclopropanecarboxylic acid [1-(2,3-dihydro-benzofuran-5-yl)-ethyl]-amide | 1.40 (a) | 342 |
| 3 | 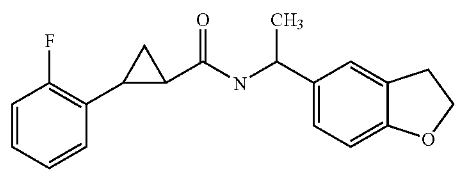 | 2-(2-Fluoro-phenyl)-cyclopropanecarboxylic acid [1-(2,3-dihydro-benzofuran-5-yl)-ethyl]-amide | 1.36 (a) | 326 |
| 4 | 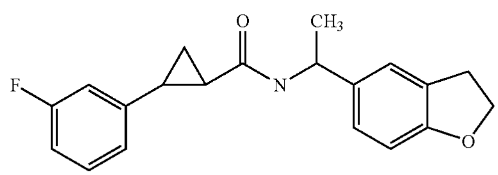 | 2-(3-Fluoro-phenyl)-cyclopropanecarboxylic acid [1-(2,3-dihydro-benzofuran-5-yl)-ethyl]-amide | 1.37 (a) | 326 |
| 5 | 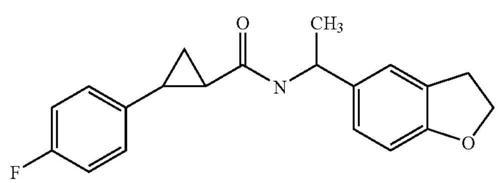 | 2-(4-Fluoro-phenyl)-cyclopropanecarboxylic acid [1-(2,3-dihydro-benzofuran-5-yl)-ethyl]-amide | 1.36 (a) | 326 |
| 6 | 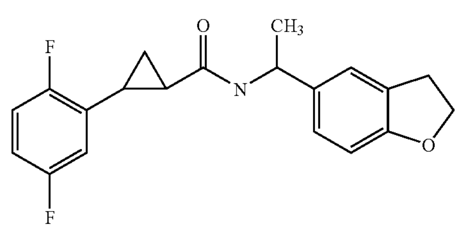 | 2-(2,5-Difluoro-phenyl)-cyclopropanecarboxylic acid [1-(2,3-dihydro-benzofuran-5-yl)-ethyl]-amide | 1.38 (a) | 344 |
| 7 | 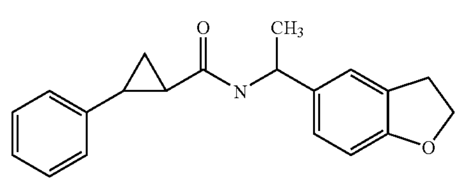 | 2-Phenyl-cyclopropanecarboxylic acid [1-(2,3-dihydro-benzofuran-5-yl)-ethyl]-amide | 1.33 (a) | 308 |

Example 8

2-Phenyl-cyclopropanecarboxylic acid(2-hydroxy-1-naphthalen-2-yl-ethyl)-amide

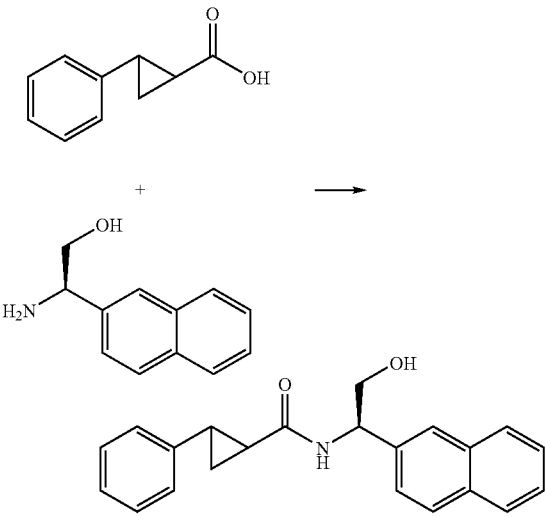

A mixture of (R)-2-amino-2-naphthalen-2-yl-ethanol (0.2 mmol), 2-phenyl-cyclopropanecarboxylic acid (0.2 mmol), EDAC.HCl (0.4 mmol), DMAP (0.2 mmol), and triethylamine (0.6 mmol) in dichloromethane (2 mL) was stirred at room temperature for 12 h. The reaction mixture was purified by flash chromatography eluting with 50% hexanes in ethyl acetate to give the desired product (52 mg) as a solid.

$^1$H NMR (400 Hz, DMSO): δ 8.67–8.65 (m, 1H), 7.88–7.84 (m, 4H), 7.49–7.46 (m, 3H), 7.29–7.19 (m, 4H), 5.05–4.92 (m, 2H), 3.67–3.63 (m, 2H), 2.18–2.06 (m, 2H), 1.30–1.17 (m, 2H).

MS (M+H)$^+$ 332.

HPLC rt: 1.39 min (method a)

Examples 9–15

Examples 9–15 were prepared from appropriate acids by the general procedure used to prepare Example 8.

| Example No. | Structure | Chemical Name | HPLC rt (min), method | Mass (M + H)$^+$ m/z |
|---|---|---|---|---|
| 9 | 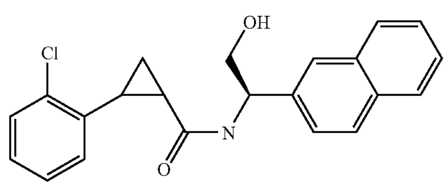 | 2-(2-Chloro-phenyl)-cyclopropanecarboxylic acid (2-hydroxy-1-naphthalen-2-yl-ethyl)-amide | 1.45 (a) | 366 |
| 10 | 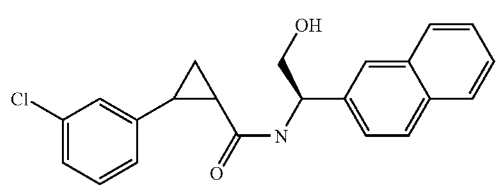 | 2-(3-Chloro-phenyl)-cyclopropanecarboxylic acid (2-hydroxy-1-naphthalen-2-yl-ethyl)-amide | 1.53 (a) | 366 |
| 11 | 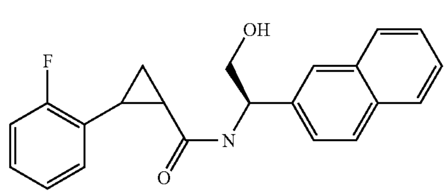 | 2-(2-Fluoro-phenyl)-cyclopropanecarboxylic acid (2-hydroxy-1-naphthalen-2-yl-ethyl)-amide | 1.39 (a) | 350 |

-continued

| Example No. | Structure | Chemical Name | HPLC rt (min), method | Mass (M + H)+ m/z |
|---|---|---|---|---|
| 12 | 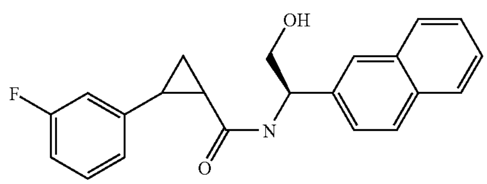 | 2-(3-Fluoro-phenyl)-cyclopropanecarboxylic acid (2-hydroxy-1-naphthalen-2-yl-ethyl)-amide | 1.43 (a) | 350 |
| 13 | 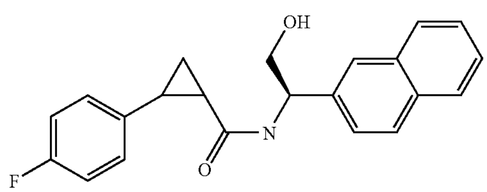 | 2-(4-Fluoro-phenyl)-cyclopropanecarboxylic acid (2-hydroxy-1-naphthalen-2-yl-ethyl)-amide | 1.40 (a) | 350 |
| 14 | 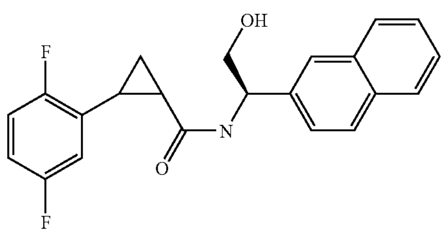 | 2-(2,5-Difluoro-phenyl)-cyclopropanecarboxylic acid (2-hydroxy-1-naphthalen-2-yl-ethyl)-amide | 1.44 (a) | 368 |
| 15 | 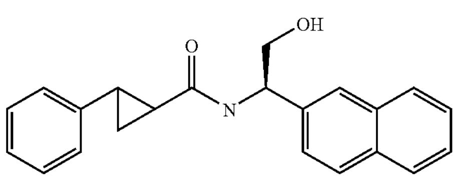 | 2-(phenyl)-cyclopropanecarboxylic acid (2-hydroxy-1-naphthalen-2-yl-ethyl)-amide | 1.39 (a) | 332 |

Example 16

2-Phenyl-cyclopropanecarboxylic acid [1-(4-fluoro-3-morpholin-4-yl-phenyl)-2-hydroxy-ethyl]-amide

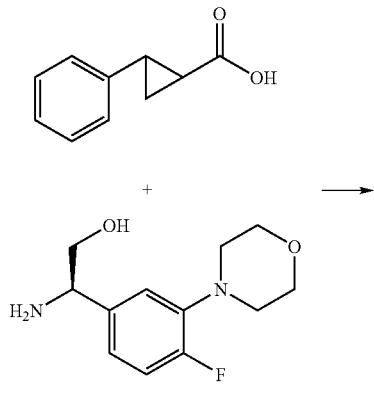

A mixture of (R)-2-amino-2-(4-fluoro-3-morpholin-4-yl-phenyl)-ethanol (0.1 mmol), 2-phenyl-cyclopropanecarboxylic acid (0.1 mmol), EDAC.HCl (0.2 mmol), DMAP (0.1 mmol), triethylamine (0.4 mmol) in dichloromethane (2 mL) was stirred at room temperature overnight. The reaction mixture was purified by flash chromatography with 3% methanol in ethyl acetate to give the desired product (27 mg) as a solid.

$^1$H NMR (400 Hz, DMSO): δ 8.53–8.47 (m, 1H), 7.28–6.96 (m, 47H), 4.86–4.84 (m, 2H), 3.75–3.70 (m, 4H), 3.52–3.50 (m, 2H), 3.00–2.97 (m, 4H), 2.25–2.15 (m, 1H), 2.04–2.01 (m, 1H), 1.35–1.17 (m, 2H).

MS (M+H)+ 385.

HPLC rt: 1.33 min (method a)

Examples 17–23

Examples 17–23 were prepared from appropriate acids by the general procedure used to prepare Example 16.

Examples 24–31

Examples 24–31 were prepared by the general procedure: A mixture of appropriate amine (0.1 mmol), appropriate

| Example No. | Structure | Name | HPLC rt (min), method | Mass (M + H)+ m/z |
|---|---|---|---|---|
| 17 | 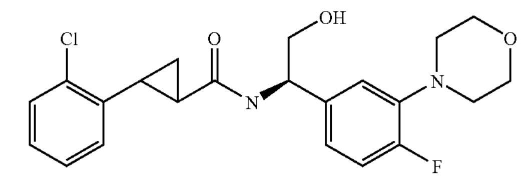 | 2-(2-Chloro-phenyl)-cyclopropanecarboxylic acid [1-(4-fluoro-3-morpholin-4-yl-phenyl)-2-hydroxy-ethyl]-amide | 1.39, 1.44 (a) | 419 |
| 18 | 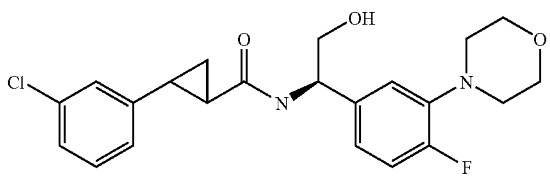 | 2-(3-Chloro-phenyl)-cyclopropanecarboxylic acid [1-(4-fluoro-3-morpholin-4-yl-phenyl)-2-hydroxy-ethyl]-amide | 1.50, 1.55 (a) | 419 |
| 19 | 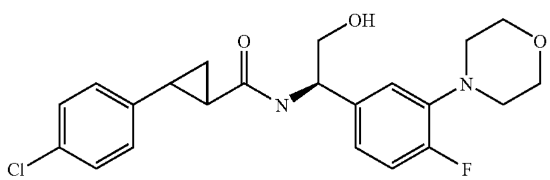 | 2-(4-Chloro-phenyl)-cyclopropanecarboxylic acid [1-(4-fluoro-3-morpholin-4-yl-phenyl)-2-hydroxy-ethyl]-amide | 1.49, 1.54 (a) | 419 |
| 20 | 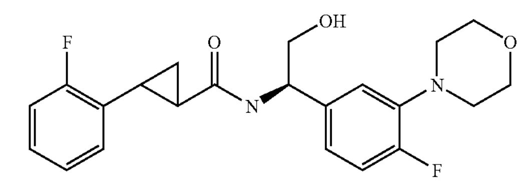 | 2-(2-Fluoro-phenyl)-cyclopropanecarboxylic acid [1-(4-fluoro-3-morpholin-4-yl-phenyl)-2-hydroxy-ethyl]-amide | 1.42 (a) | 403 |
| 21 | 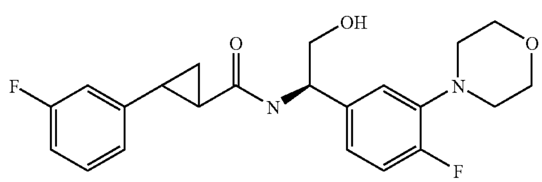 | 2-(3-Fluoro-phenyl)-cyclopropanecarboxylic acid [1-(4-fluoro-3-morpholin-4-yl-phenyl)-2-hydroxy-ethyl]-amide | 1.39 (a) | 403 |
| 22 | 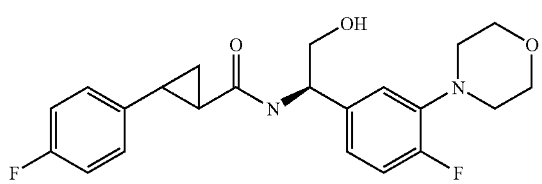 | 2-(4-Fluoro-phenyl)-cyclopropanecarboxylic acid [1-(4-fluoro-3-morpholin-4-yl-phenyl)-2-hydroxy-ethyl]-amide | 1.38 (a) | 403 |
| 23 | | 2-(2,5-Difluoro-phenyl)-cyclopropanecarboxylic acid [1-(4-fluoro-3-morpholin-4-yl-phenyl)-2-hydroxy-ethyl]-amide | 1.38 (a) | 421 | cinnamic acid (0.1 mmol), EDC.HCl (0.2 mmol), DMAP (0.2 mmol), and triethylamine (0.4 mmol) in dichloromethane (2 mL) was stirred at room temperature for 12 h. The reaction mixture was purified by flash chromatography with 50% hexanes in ethyl acetate to give the titled compounds.

| Example No. | Structure | Chemical name | HPLC rt (min), method | Mass (M + H)+ m/z |
|---|---|---|---|---|
| 24 | 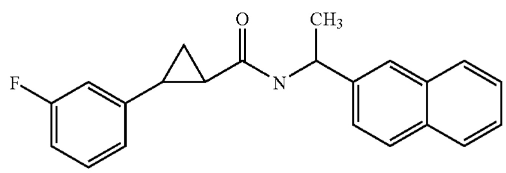 | 2-(3-Fluoro-phenyl)-cyclopropanecarboxylic acid (1-naphthalen-2-yl-ethyl)-amide | 1.54 (a) | 334 |
| 25 | 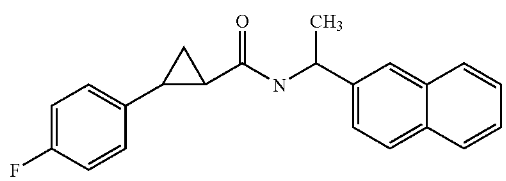 | 2-(4-Fluoro-phenyl)-cyclopropanecarboxylic acid (1-naphthalen-2-yl-ethyl)-amide | 1.62 (a) | 334 |
| 26 | 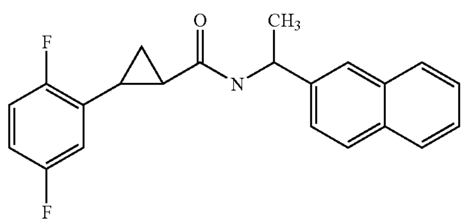 | 2-(2,5-Difluoro-phenyl)-cyclopropanecarboxylic acid (1-naphthalen-2-yl-ethyl)-amide | 1.56 (a) | 352 |
| 27 | 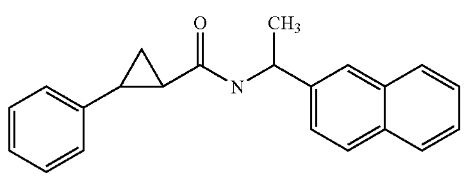 | 2-Phenyl-cyclopropanecarboxylic acid (1-naphthalen-2-yl-ethyl)-amide | 1.53 (a) | 316 |
| 28 | 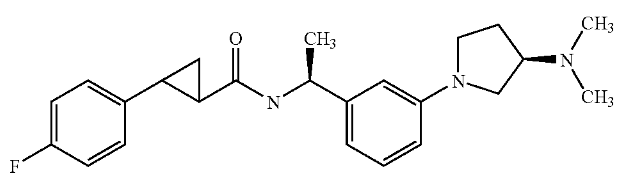 | 2-(4-Fluoro-phenyl)-cyclopropanecarboxylic acid {1-[3-(3-dimethylamino-pyrrolidin-1-yl)-phenyl]-ethyl}-amide | 1.15 (a) | 396 |
| 29 | 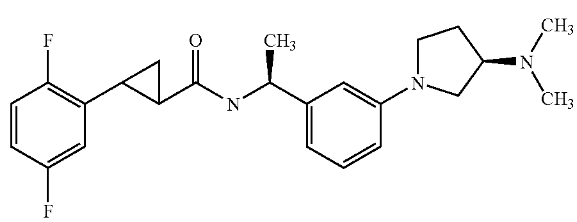 | 2-(2,5-Difluoro-phenyl)-cyclopropanecarboxylic acid {1-[3-(3-dimethylamino-pyrrolidin-1-yl)-phenyl]-ethyl}-amide | 1.10, 1.15 (a) | 413 |
| 30 | 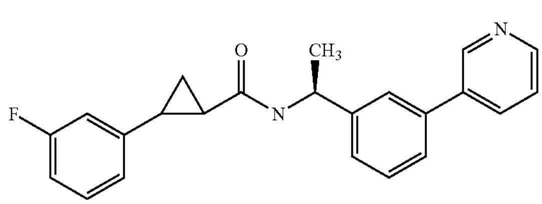 | 2-(3-Fluoro-phenyl)-cyclopropanecarboxylic acid [1-(3-pyridin-3-yl-phenyl)-ethyl]-amide | 1.08 (a) | 361 |

| Example No. | Structure | Chemical name | HPLC rt (min), method | Mass (M + H)+ m/z |
|---|---|---|---|---|
| 31 | 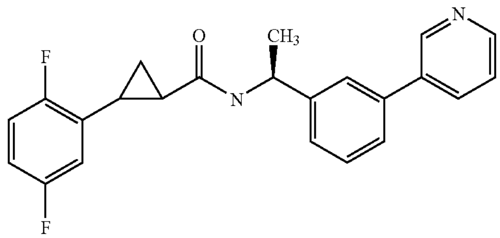 | 2-(2,5-Difluoro-phenyl)-cyclopropanecarboxylic acid [1-(3-pyridin-3-yl-phenyl)-ethyl]-amide | 1.09 (a) | 379 |

Examples 32–36

Examples 32–36 were prepared by the general procedure: A mixture of the appropriate cinnamic acid (0.083 mmol), (S)-1-(3-pyridin-3-yl-phenyl)-ethylamine (12.7 mg, 0.064 mmol), EDAC (18.4 mg, 0.096 mmol), HOBT (13 mg, 0.096 mmol), DMF (2 mL) and diisopropylethylamine (33 μL, 0.192 mmol) was stirred at 23° C. for 18 h. The residue was purified by preparative HPLC (Primeshere C18-HC 21.2×100 mm; (5 mM $NH_4OAc$) 0–100% gradient over 5 min; 20 mL/min flow rate) to afford the titled products.

| Example No. | Structure | Chemical name | HPLC rt (min), method | Mass (M + H)+ m/z |
|---|---|---|---|---|
| 32 | 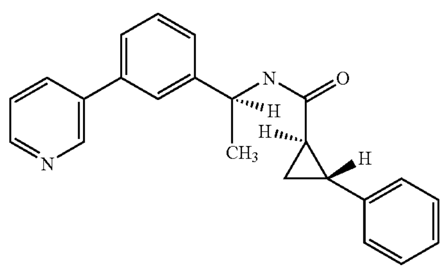 | (S)-2-Phenyl-cyclopropanecarboxylic acid [1-(3-pyridin-3-yl-phenyl)-ethyl]-amide | 1.75 (b) | 343 |
| 33 | 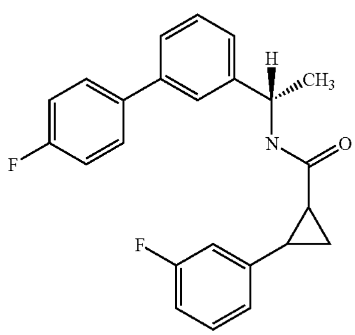 | (S)-2-(3-Fluoro-phenyl)-cyclopropanecarboxylic acid {1-[3-(6-fluoro-pyridin-3-yl)-phenyl]-ethyl}-amide | 1.95 (b) | 379 |
| 34 | 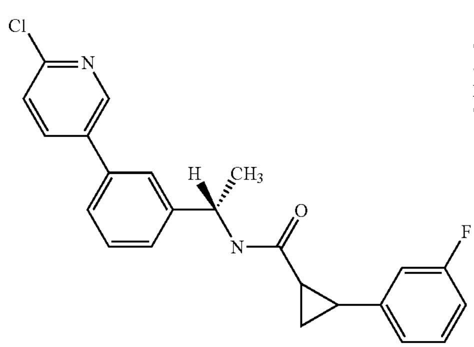 | (S)-2-(3-Fluoro-phenyl)-cyclopropanecarboxylic acid {1-[3-(6-chloro-pyridin-3-yl)-phenyl]-ethyl}-amide | 2.00 (b) | 395 |

-continued

| Example No. | Structure | Chemical name | HPLC rt (min), method | Mass (M + H)+ m/z |
|---|---|---|---|---|
| 35 | 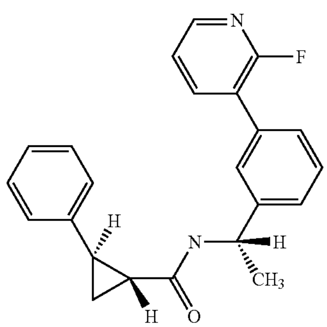 | (S)-2-Phenyl-cyclopropanecarboxylic acid {1-[3-(2-fluoro-pyridin-3-yl)-phenyl]-ethyl}-amide | 1.87 (c) | 361 |
| 36 | 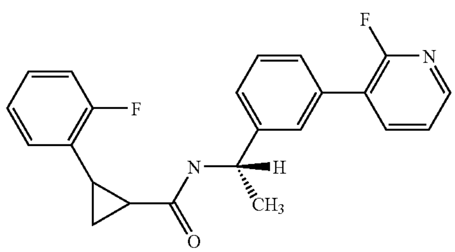 | (S)-2-(2-Fluoro-phenyl)-cyclopropanecarboxylic acid {1-[3-(2-fluoro-pyridin-3-yl)-phenyl]-ethyl}-amide | 1.91 (c) | 379 |

What is claimed is:

1. A compound of Formula I or a pharmaceutically acceptable salt thereof

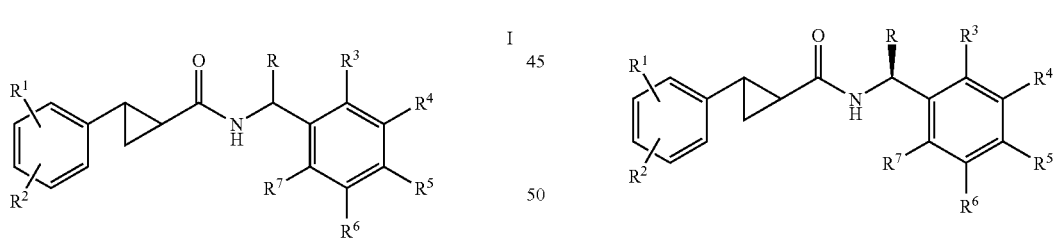

wherein
R is $C_{1-4}$ alkyl, $CF_3$ or hydroxymethyl;
$R^1$ and $R^2$ are each independently hydrogen, $C_{1-4}$ alkyl, halogen or morpholin-4-yl;
$R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro;
$R^5$ is hydrogen or fluoro; or $R^4$ and $R^5$ taken together are —CH=CH—CH=CH— or —CH$_2$CH$_2$O—; and
$R^3$, $R^6$ and $R^7$ are each independently selected from hydrogen or fluoro.

2. The compound of claim 1 having the Formula Ic or a pharmaceutically acceptable salt thereof wherein
R is methyl or hydroxymethyl;
$R^1$ and $R^2$ are each independently hydrogen, $C_{1-4}$ alkyl, halogen or morpholin-4-yl;
$R^4$ is selected from the group consisting of optionally substituted morpholin-4-yl, pyridinyl, pyrimidinyl, piperazinyl, and pyrazinyl, in which said substituent is independently selected from the group consisting of $C_{1-4}$alkyl, dimethylamino, hydroxymethyl, chloro and fluoro;
$R^5$ is hydrogen or fluoro; or $R^4$ and $R^5$ taken together are —CH=CH—CH=CH— or —CH$_2$CH$_2$O—; and
$R^3$, $R^6$ and $R^7$ are each independently selected from hydrogen or fluoro.

3. The compound of claim 1 selected from the group consisting of:
  2-(2-fluoro-phenyl)-cyclopropanecarboxylic acid[1-(2,3-dihydro-benzofuran-5-yl)-ethyl]-amide;
  2-(3-fluoro-phenyl)-cyclopropanecarboxylic acid[1-(2,3-dihydro-benzofuran-5-yl)-ethyl]-amide;
  2-(4-fluoro-phenyl)-cyclopropanecarboxylic acid[1-(2,3-dihydro-benzofuran-5-yl)-ethyl]-amide;
  2-(2-fluoro-phenyl)-cyclopropanecarboxylic acid(2-hydroxy-1-naphthalen-2-yl-ethyl)-amide;
  2-(3-fluoro-phenyl)-cyclopropanecarboxylic acid(2-hydroxy-1-naphthalen-2-yl-ethyl)-amide;
  2-(4-fluoro-phenyl)-cyclopropanecarboxylic acid(2-hydroxy-1-naphthalen-2-yl-ethyl)-amide;
  2-(2,5-difluoro-phenyl)-cyclopropanecarboxylic acid(2-hydroxy-1-naphthalen-2-yl-ethyl)-amide;
  2-(2-fluoro-phenyl)-cyclopropanecarboxylic acid[1-(4-fluoro-3-morpholin-4-yl-phenyl)-2-hydroxy-ethyl]-amide;
  2-(3-fluoro-phenyl)-cyclopropanecarboxylic acid[1-(4-fluoro-3-morpholin-4-yl-phenyl)-2-hydroxy-ethyl]-amide;
  2-(4-fluoro-phenyl)-cyclopropanecarboxylic acid[1-(4-fluoro-3-morpholin-4-yl-phenyl)-2-hydroxy-ethyl]-amide;
  2-(2,5-difluoro-phenyl)-cyclopropanecarboxylic acid[1-(4-fluoro-3-morpholin-4-yl-phenyl)-2-hydroxy-ethyl]-amide;
  2-(4-fluoro-phenyl)-cyclopropanecarboxylic acid(1-naphthalen-2-yl-ethyl)-amide;
  2-(2,5-difluoro-phenyl)-cyclopropanecarboxylic acid(1-naphthalen-2-yl-ethyl)-amide;
  2-(4-fluoro-phenyl)-cyclopropanecarboxylic acid{1-[3-(3-dimethylamino-pyrrolidin-1-yl)-phenyl]-ethyl1}-amide;
  2-(2,5-difluoro-phenyl)-cyclopropanecarboxylic acid{1-[3-(3-dimethylamino-pyrrolidin-1-yl)-phenyl]-ethyl}-amide;
  2-(3-fluoro-phenyl)-cyclopropanecarboxylic acid[1-(3-pyridin-3-yl-phenyl)-ethyl]-amide;
  2-(2,5-difluoro-phenyl)-cyclopropanecarboxylic acid[1-(3-pyridin-3-yl-phenyl)-ethyl]-amide;
  (S)-2-phenyl-cyclopropanecarboxylic acid[1-(3-pyridin-3-yl-phenyl)-ethyl]-amide;
  (S)-2-(3-fluoro-phenyl)-cyclopropanecarboxylic acid{1-[3-(6-fluoro-pyridin-3-yl)-phenyl]-ethyl}-amide;
  (S)-2-phenyl-cyclopropanecarboxylic acid{1-[3-(2-fluoro-pyridin-3-yl)-phenyl]-ethyl}-amide; and
  (S)-2-(2-fluoro-phenyl)-cyclopropanecarboxylic acid{1-[3-(2-fluoro-pyridin-3-yl)-phenyl]-ethyl}-amide;
  or a pharmaceutically acceptable salt thereof.

4. A pharmaceutical composition comprising a therapeutically effective amount of the compound of claim 1 in association with a pharmaceutically acceptable carrier, adjuvant or diluent.

5. A method for the treatment of disorders responsive to opening of the KCNQ potassium channels in a mammal in need thereof wherein said disorders are acute and chronic pain, migraine, neuropathic pain, bipolar disorders, convulsions, mania, epilepsy, anxiety and depression, which comprises administering to said mammal a therapeutivally effective amount of the compound of claim 1.

6. The method of claim 5 wherein said disorder is migraine.

7. The method of claim 5 wherein said disorder is neuropathic pain.

* * * * *